US005476659A

United States Patent [19]
Goodman et al.

[11] Patent Number: 5,476,659
[45] Date of Patent: Dec. 19, 1995

[54] CANCEROUS B CELL TREATMENT USING SUBSTITUTED NUCLEOSIDE DERIVATIVES

[75] Inventors: Michael G. Goodman, Rancho Santa Fe; Lawrence D. Piro, La Jolla, both of Calif.

[73] Assignee: The Scripps Research Institute, La Jolla, Calif.

[21] Appl. No.: 151,142

[22] Filed: Nov. 12, 1993

Related U.S. Application Data

[63] Continuation-in-part of Ser. No. 975,830, Nov. 13, 1992, abandoned, which is a continuation-in-part of Ser. No. 945,215, Sep. 15, 1992, Pat. No. 5,317,013, which is a division of Ser. No. 562,101, Aug. 2, 1990, Pat. No. 5,147,636, which is a division of Ser. No. 361,974, Jun. 9, 1989, Pat. No. 4,948,730, which is a division of Ser. No. 14,618, Feb. 13, 1987, Pat. No. 4,849,411, which is a continuation of Ser. No. 546,679, Nov. 1, 1983, Pat. No. 4,643,992, which is a continuation-in-part of Ser. No. 439,846, Nov. 9, 1982, Pat. No. 4,539,205.

[51] Int. Cl.⁶ .......................... A61K 39/39; A61K 31/70; C12N 5/06; C12N 5/08
[52] U.S. Cl. .......................... 424/278.1; 514/45; 514/908; 435/240.2
[58] Field of Search .................. 514/26, 34, 45, 514/171, 188, 885, 908; 424/178.1, 181.1, 278.1; 435/240.2

[56] References Cited

U.S. PATENT DOCUMENTS

| | | | |
|---|---|---|---|
| 4,539,205 | 9/1985 | Goodman et al. | 514/45 |
| 4,596,676 | 6/1986 | Cullinan | 540/478 |
| 4,643,992 | 2/1987 | Goodman et al. | 514/45 |
| 4,724,213 | 2/1988 | Epstein | 424/1.49 |
| 4,746,651 | 5/1988 | Goodman | 514/45 |
| 4,801,688 | 1/1989 | Laguzza et al. | 530/391.9 |
| 4,814,438 | 3/1989 | Armour et al. | 536/27.23 |
| 4,861,579 | 8/1989 | Meyer, Jr. et al. | 424/1.53 |
| 4,948,730 | 8/1990 | Goodman et al. | 435/70.5 |
| 5,166,141 | 11/1992 | Goodman et al. | 514/45 |
| 5,317,013 | 5/1994 | Goodman et al. | 514/45 |

OTHER PUBLICATIONS

Goodman et al., (1991) Blood 78(suppl. 1)=437(a) Abstr. No. 1738.

*Primary Examiner*—Kay K. A. Kim
*Attorney, Agent, or Firm*—Welsh & Katz, Ltd.

[57] ABSTRACT

Processes for the killing of cancerous B cells, and particularly chronic lymphocytic leukemia (CLL) cells are disclosed. In one process, cancerous B cells that do not proliferate when contacted with an immune response-enhancing agent are contacted with an amount of such an agent sufficient to cause peripheral CLL cells to undergo blast transformation and proliferation. The contacted cells are then maintained for a time period sufficient for them to die from that contact. Further contacting of those cells with a cytotoxic amount of an anti-cancer drug or cytotoxic conjugate enhances the death of those cancer cells. In another process, peripheral CLL cells that proliferate on contact with an immune response-enhancing-agent are contacted with a proliferation-inducing amount of such an agent. The contacted cells are maintained for a time period sufficient to undergo blast transformation and proliferation, and the blasts are then contacted with a cytotoxic amount of an anti-cancer drug or cytotoxic conjugate and maintained.

32 Claims, 7 Drawing Sheets

1

CANCEROUS B CELL TREATMENT USING SUBSTITUTED NUCLEOSIDE DERIVATIVES

This invention was made with government support under Contrast No. AI 15284 by the National Institutes of Health. The government has certain rights in the invention.

DESCRIPTION

Cross-Reference to Applications

This is a continuation-in-part of application Ser. No. 07/975,830, filed Nov. 13, 1992, that was a continuation-in-part of application, Ser. No. 945,215, filed Sep. 15, ,01992, now U.S. Pat. No. 5,317,013, that was a division of application Ser. No. 562,101, filed Aug. 2, 1990, now U.S. Pat. No. 5,147,636, that was a division of application Ser. No. 361,974, filed Jun. 9, 1989, now U.S. Pat. No. 4,948,730, that was division of application Ser. No. 014,618, filed Feb. 13, 1987, now U.S. Pat. No. 4,849,411, that was a continuation of application Ser. No. 546,679, filed Nov. 1, 1983, now U.S. Pat. No. 4,643,992, that was a continuation-in-part of application Ser. No. 439,846, filed Nov. 9, 1982, now U.S. Pat. No. 4,539,205.

TECHNICAL FIELD

This invention relates to the killing of cancerous B cells, and more particularly to the killing of such cells by a nucleoside derivative alone or in concert with a standard anti-cancer drug.

BACKGROUND ART

Cancers of the B cell such as lymphomas and leukemias are relatively prevalent human diseases. Of those cancers, chronic lymphocytic leukemia (CLL) is the most prevalent, with about 10,000 new cases being diagnosed each year. CLL accounts for about 30 percent of leukemias in western countries.

In addition to CLL, there are several other B cell cancers. Included among those additional B cell cancers are non-Hodgkin's lymphomas, hairy cell leukemia, plasmacytomas, plasma cell leukemia, multiple myelomas and Hodgkin's lymphomas. Similar cancers are often present in other mammalian hosts, such as the mouse, where, for example the $BCL_1$ $5B_1b$ cell line has similarity to CLL cell subsets.

Treatments for these cancers have varying degrees of effectiveness. For example, hairy cell leukemia, which affects relatively few people, has recently been very effectively treated with 2-chloro-2'-deoxyadenosine. A typical treatment for CLL uses chlorambucil as the usual first anti-cancer drug of choice and sometimes adds a glucosteroid such as prednisone or dexamethasone. However, patients at intermediate to high risk levels with this form of cancer have median survivals of six and two years, respectively, and those two classes of the disease constitute about 70 percent of the cases.

CLL cells proliferate quite slowly, and as a result, cytotoxic anti-cancer drugs that act at specific stages in the cell cycle and can thus act preferentially on rapidly proliferating cells, are rendered minimally effective in this disease. To date, except for a preliminary report by the inventors herein [Goodman and Piro, *Blood*, 78:437a (Suppl. 1) (Nov. 15, 1991)], there has been no report of inducing the proliferation of CLL cells with a chemotherapeutic agent that is pharmaceutically useful. The chemotherapeutic agent used in that work was loxoribine; 7-allyl-8-oxoguanosine.

Co-assigned U.S. Pat. No. 4,539,205 to Goodman and Weigle describes modulation of animal cellular responses with S-substituted guanine derivatives bonded 9-1' to an aldose having 5 or 6 carbon atoms in the aldose chain (ring). The cellular modulations described in that patent relate mostly to immunomodulation such as adjuvanticity in producing primary and secondary immune responses. Activity against certain neoplastic conditions is also disclosed as are T cell-replacing activity, an IL-I like activity on thymocytes, and induction of the release of lysosomal enzymes from neutrophils. The 8-substituents in those molecules have electron withdrawing inductive effects relative to hydrogen. Thus, halo, mercapto or its thioxo tautomer, acyl mercapto, alkyl sulfido, nitro, cyano, keto, halomethyl and methyleneoxy alkyl and the like were disclosed as useful, while electron donating substituents such as an amino group were found to be inactive.

In addition, co-assigned, U.S. Pat. No. 4,643,992 its continuation, U.S. Pat. No. 4,849,411, and divisional U.S. Pat. Nos. 4,948,730, 5,147,636, and U.S. patent application Ser. No. 07/945,215, filed Sep. 15, 1992, further disclose the use of derivatives of 8-hydroxyguanine (8-oxoguanine), 7-methyl-8-oxoguanine and 7-methyl-8 -thioxo-guanine in modulating animal immune responses. Further results using guanine derivatives disclosed in U.S. Pat. No. 4,539,205 are also disclosed as are similar results using guanine derivatives disclosed for the first time in that application.

U.S. Pat. No. 3,798,210 to Pfleiderer describes the synthesis of 8-(1'-glycosidyl)-pteridines, including isoxanthopterin derivatives. That patent teaches the use of its compounds as the active pharmaceutical agents against specific pathogens such as malaria and tubercle bacilli, pathogenic fungi, gram-positive and gram-negative bacteria, and primarily against viruses such as herpes virus and influenza virus. Some of the compounds of the Pfleiderer patent are also useful herein, not as antibiotics as is taught in Pfleiderer, but as an immune response-enhancing agent. This use is described hereinafter.

Co-assigned U.S. Pat. No. 4,746,651 discloses the antimicrobial use of an antibiotic and a potentiating amount of a guanosine compound or isoxanthopterin as described in the above patents and those discussed hereinafter. Thus, U.S. Pat. Nos. 5,011,828 and 5,093,318 disclose immune response-enhancing guanosine derivatives having an =O, =S, =Se and =NCN groups at the 8-position of a guanine nucleoside and a hydrocarbyl or heteroatom-substituted hydrocarbyl group at the 7-position of the guanine ring. U.S. Pat. Nos. 4,880,784 and 5,166,141 disclose 7-oxa- and 7-thia-guanosines having an =O or =S group at the 8-position of the ring.

BRIEF SUMMARY OF THE INVENTION

Two related processes for killing cancerous B cells are contemplated herein. A first process comprises contacting in an aqueous medium a potentiating (CLL cell proliferating) amount of an immune response-enhancing agent with cancerous B cells of a host mammal that do not proliferate and undergo blast transformation when contacted with a proliferation-inducing amount of an immune response-enhancing agent. That contact is maintained under biological culture conditions for a time period sufficient for the contacted cancerous B cells to die. The immune response-enhancing agent has a structure that corresponds to a formula shown below.

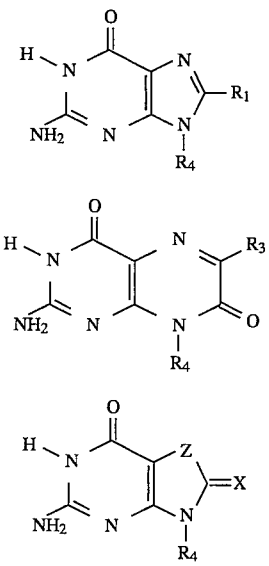

wherein

Z is O, S or N—$R_2$;

$R_1$ contains up to about 20 atoms and has a Hammett substituent sigma constant for ionization of a meta-substituted benzoic acid that is greater than that of hydrogen;

$R_1$ is a radical having a length up to about that of an n-decyl group that is selected from the group consisting of $C_1$–$C_{10}$ alkyl (more preferably $C_1$–$C_6$ alkyl, and most preferably $C_3$–$C_6$ alkyl), $C_3$–$C_{10}$ beta-alkenyl, phenyl-substituted $C_3$–$C_6$ beta-alkenyl, benzyl, $C_1$–$C_6$ alkoxybenzyl, nitrobenzyl, hydroxy $C_1$–$C_{10}$ alkyl, polyhydroxy $C_1$–$C_{10}$ alkyl, halo $C_1$–$C_{10}$ alkyl, polyhalo $C_1$–$C_{10}$ alkyl, $C_1$–$C_6$ alkylene $C_1$–$C_6$ alkylcarboxylate, $C_1$–$C_{10}$ alkanoyl, $C_1$–$C_6$ alkoxy $C_1$–$C_6$ alkylenecarbonyl, and $C_1$–$C_6$ alkylenecarboxamido in which the carboxamido group has the formula $CONR_9R_{10}$ wherein $R_9$ and $R_{10}$ are the same or different and are selected from the group consisting of hydrogen and $C_1$–$C_6$ alkyl, or $NR_9R_{10}$ together form a heterocyclic ring having five or six atoms in the ring;

X is oxygen or sulfur;

$R_3$ is a radical selected from the group consisting of hydrogen, $C_1$–$C_6$ alkyl, hydroxy $C_1$–$C_6$ alkyl, polyhydroxy $C_1$–$C_6$ alkyl, phenyl, phenyl-$C_1$–$C_6$ alkylene, $C_1$–$C_6$ alkylphenyl, $C_1$–$C_6$ alkoxyphenyl, halophenyl, trifluoromethylphenyl, hydroxy, oxo (O=), $C_1$–$C_6$ alkoxy, phenyl-$C_1$–$C_6$ alkoxy, halo, mercapto, thioxo (S=), $C_1$–$C_6$ alkylthio, phenyl-$C_1$–$C_6$ alkylthio, $C_1$–$C_6$ alkanoyl ($C_1$–$C_6$ acyl), $C_1$–$C_6$ alkoxy carbonyl, $C_1$–$C_6$ alkylene $C_1$–$C_6$ alkylcarboxylate, $C_1$–$C_6$ alkoxy $C_1$–$C_6$ alkyl carbonyl, and $C_1$–$C_6$ alkyl carboxamido in which the carboxamido group has the formula $CONR_9R_{10}$ wherein $R_9$ and $R_{10}$ are the same or different and are selected from the group consisting of hydrogen and $C_1$–$C_6$ alkyl, or $NR_9R_{10}$ together form a heterocyclic ring having five or six atoms in the ring;

$R_4$ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl, and their O-substituted $C_1$–$C_6$ alkyl, $C_1$–$C_6$ alkanoyl, benzyl, benzoyl and $C_1$–$C_6$ acetal or ketal derivatives. Preferably an O-substituent other than an acetal or ketal, if present on one oxygen, is present on all available ring substituent oxygens;

the pharmaceutically acceptable salts of said agent; and the tautomers thereof. A contemplated immune response-enhancing agent is free from ionic charge in water at a pH value of 7.2–7.4; i.e., at physiological pH values.

The above contacting is preferably repeated a plurality of times. A synergistic cytotoxic effect has also been found where a usually used anti-cancer drug is administered to contact those cells about 2 to about 4 days after contact by the immune response-enhancing agent. Particularly preferred immune response-enhancing agents include 7-allyl-8-oxoguanosine ($R_4$ is β9,1'-ribofuranosyl, =X is =O and Z is N—$R_2$ wherein $R_2$ is allyl), 7-(2-chloroethyl)-8-oxoguanosine ($R_4$ is β9,1'-ribofuranosyl, =X is =O and Z is N—$R_2$ where $R_2$ is 2-chloroethyl), and 8-mercaptoguanosine ($R_4$ is β9,1'-ribofuranosyl and $R_1$ is SH or =S).

The second process is directed more specifically to cancerous B cell disease states such as CLL where cells proliferate and undergo blast transformation upon being contacted with an immune response-enhancing agent. Here, CLL cells of a host mammal that proliferate and undergo blast transformation when contacted with an immune response-enhancing agent are contacted in an aqueous medium with a potentiating (proliferation-inducing) amount of an immune response-enhancing agent. That contact is maintained under biological culture conditions for a time period sufficient for the contacted CLL cells to enter the cell cycle, begin to undergo blast transformation and proliferate. The cells so treated are then contacted with a cytotoxic amount of an anti-cancer drug. That contact is maintained under biological culture conditions for a time period sufficient for the contacted cells to die. The immune response-enhancing agent used is that discussed before.

The anti-cancer drug used in either process can be one or more of those usually used to treat various types of cancers, and particularly B cell cancers. Such drugs are used in their usual dosages and administration regimens. Particularly preferred immune response-enhancing agents used in the above process are the same as those discussed for the first process.

BRIEF DESCRIPTION OF THE DRAWINGS

In the drawings forming a portion of this disclosure.

DETAILED DESCRIPTION OF THE INVENTION

A. The Processes

Figure 1:
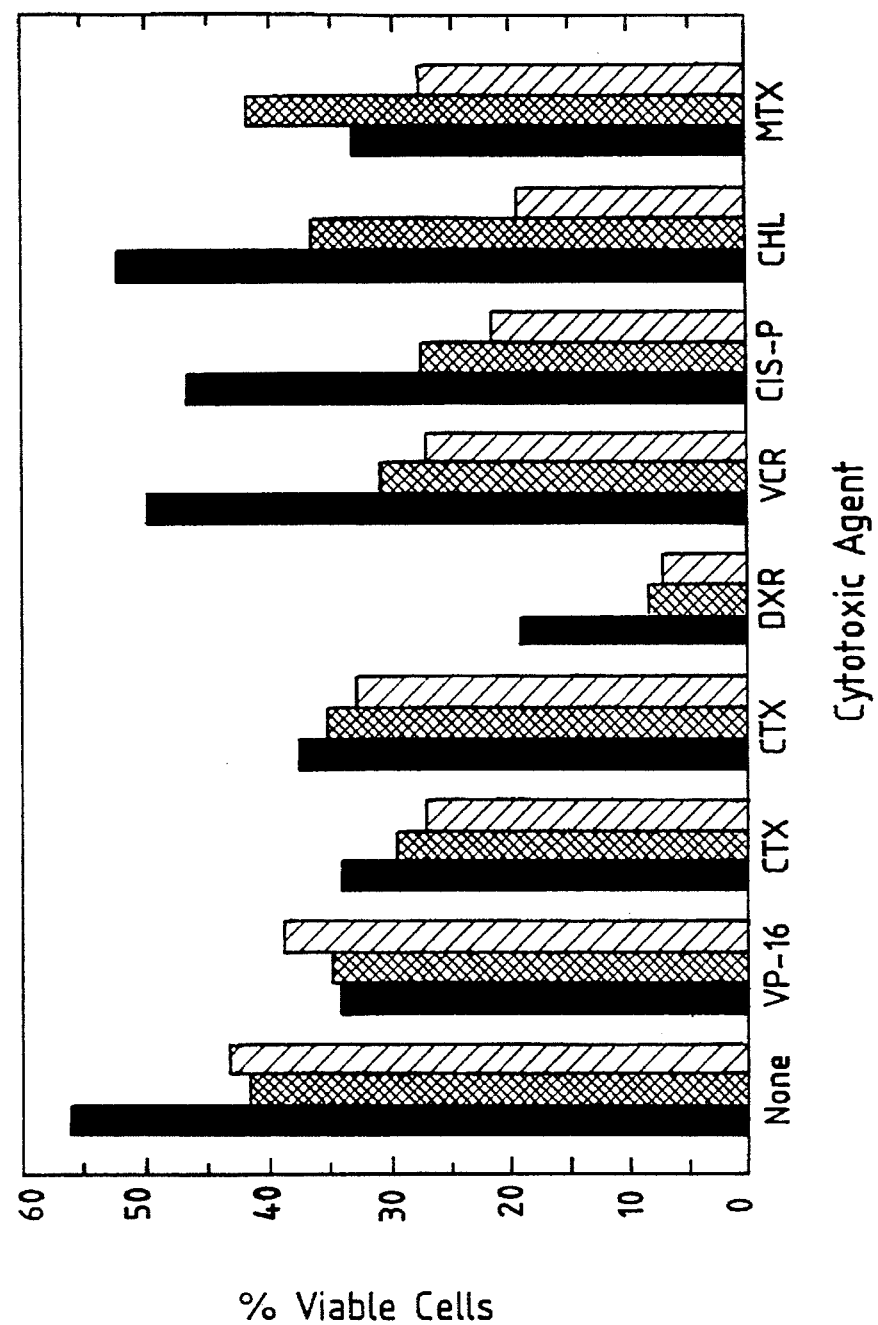
FIG. 1 illustrates the results of two-stage viability assays performed as described in Example 2. Briefly, a CLL patient's peripheral CLL cells that do not undergo blast transformation and proliferation when contacted with loxoribine were maintained for two days in contact with loxoribine at either 0.3 mM or 1.0 mM followed by one additional day in contact with an anti-cancer drug (cytotoxic agent) for a total of three days from initiation of the culture. The anti-cancer drugs are listed from left to right on the x-axis as follows, with the drug names and final concentrations being shown in parentheses: VP-16 (etoposide; 10 μg/ml); CTX (cytoxan; $10^{-6}$M); DXR (adriamycin; $10^{-5}$M); VCR (vincristine; $10^{-6}$M); CIS-P (cisplatin; $10^{-5}$M); CHL (chlorambucil; $10^{-5}$M), and MTX (methotrexate; $10^{-6}$M). The data are plotted in a bar graph where percentage of viable cells is plotted on the Y-axis against the assayed anti-cancer drug with loxoribine (0.3 mM in the crosshatched bars or 1.0 mM in the diagonally lined bars) or without loxoribine (blackened bars). The data are compared to cells either untreated or uncontacted with anti-cancer drug (indicated as "none" on the graph).

It has been found that upon contact of CLL cells with an immune response-enhancing agent described herein that one or both of two phenomena occur.

In cultured cells from most patients, the normally quiescent, relatively small cancerous cells enlarge in size about 2–5 fold, develop very large prominent nucleoli, and develop an open, dispersed chromatin pattern as compared with the dense, clumped pattern seen in control cells. These changes take place in vitro upon 1–3 days of culture.

The quiescent cancerous cells thus change into blastic, proliferative cells with an accompanying marked increase in uptake of DNA precursors such as radio-labeled thymidine. This change in DNA precursor uptake is similar to that seen where an immune response-enhancing agent useful herein is used as a mitigen in mouse B cell-containing preparations described in several of the before-mentioned patents. Most samples of normal human B cells do not respond mitogenically to these immune-response enhancing agents.

The second effect seen on such contacting of CLL cells from about 20 to about 25 percent of the patients studied and certain other cancerous B cells is essentially no proliferative response during the same 1–3 days in vitro culture period. However, after about 6 to about 23 days of culture, the loxoribine contacted cells such as CLL cells die to an extent greater than control cells cultured similarly. Cancerous cells such as mouse $BCL_1$ lymphoma and P388 neoplastic lymphoid cells and some human CLL cells can normally be cultured substantially indefinitely.

It is further noted that often the CLL cells that proliferate and transform into blasts, when contacted with an immune response-enhancing agent also die more rapidly than do eLL cells that are not so contacted. Thus, the mechanism that operates to kill the non-proliferating cells may also be operative in the proliferating cells.

Some CLL patients have cancerous cells of both types. That is, some of their cancerous CLL cells proliferate and transform into blasts, whereas others do not.

The mechanism by which proliferation is initiated in normally quiescent CLL cells and the mechanism by which both the proliferating and non-proliferating CLL cells and other cancerous B cells die more quickly after contact are not known. Without wishing to be bound by theory, a possible explanation for the delayed death of such contacted cells may relate to apoptosis and the bcl2 or similar proto-oncogene product that is present in CLL and other cancer cells.

Thus, it is thought that the bcl-2 oncogene and its protein product may cause the long life of those cancerous cells by inhibiting apoptosis. Contacting the cells that do not proliferate and undergo blast transformation with a CLL proliferation-inducing amount of an immune response-enhancing agent as described herein may inhibit expression or the activity of the bcl-2 or other oncogene, thereby causing the death of an otherwise substantially immortal cell. This mechanism may also be operant in CLL and other B cell cancer cells that proliferate in response to loxoribine.

One aspect of the invention contemplates contacting in an aqueous medium with a CLL cell potentiating (proliferation-inducing) amount of an immune response-enhancing agent with cancerous B cells of a host mammal that do not proliferate and undergo blast transformation when contacted with an immune response-enhancing agent. That contact is maintained under biological culture conditions for a time sufficient for the contacted cancerous cells to die. The time to death for the contacted cells is shorter than the time required for non-contacted cells to die under similar conditions.

In a preferred variant of this aspect, the cancerous B cells are further contacted with a cytotoxic amount of an anti-cancer drug, and the anti-cancer drug-contacted cells are maintained under biological culture conditions for a period of time sufficient for those cells to die. This contacting is carried out about 1 to about 4 days after the first contacting with the immune response-enhancing agent. Thus, even though these cells do not proliferate and undergo blast transformation, standard anti-cancer drug treatment synergizes with the effect caused by the immune response-enhancing agent to more effectively kill the cells.

In another aspect, a process of the invention contemplates contacting in an aqueous medium CLL cells of a host mammal that proliferate and undergo blast transformation when contacted with an immune response-enhancing agent using a potentiating (proliferation-inducing) amount of an immune response-enhancing agent discussed herein. That contact is maintained under biological culture conditions and for a time period sufficient for the contacted CLL cells to enter the cell cycle and begin to undergo blast transformation. The treated cells are then contacted with a cytotoxic amount of an anti-cancer drug and maintained under biological culture conditions for a time period sufficient for the contacted cells to die.

The above, first process is directed to cancerous B cells that do no proliferate and undergo blast transformation. That process is useful for substantially every type of cancerous condition of B cells; e.g., a B cell lymphoma or leukemia. Particular examples include the non-proliferating, cancerous cells of a human CLL patient, human hairy cell leukemia cells, cells of patients with certain non-Hodgkin's lymphomas, plasmacytomas, plasma cell leukemia, multiple myeloma, and Hodgkin's lymphomas, mouse $BCL_1$ B cell lymphoma cells (such as ATCC TIB 197), and even hybridoma cells that are the fusion product of a non-cancerous B cell and a myeloma cell such as hybridoma M1/70 that secretes monoclonal antibodies to monocytes (such as ATCC TIB 128). Cells from other exemplary mammalian host cancerous B cell lines are available from the American Type Culture Collection (ATCC), 12301 Parklawn Drive, Rockville, Md. 20852, as well as from other sources well known to skilled workers.

In accordance with either process discussed before, cells that do or do not undergo cell cycle entry, blast transformation and proliferation in the presence of a CLL cell proliferation-inducing amount of an immune response-enhancing agent are contacted with that amount of that agent. Thus, even though the particular cancerous B cells that are contacted may not themselves undergo cell cycle entry, blast transformation and proliferation, those cancerous B cells are contacted with an amount of an immune response-enhancing agent that causes responsive CLL cells to undergo cell cycle entry, blast transformation and proliferation. That amount is determined separately as discussed hereinafter.

Whether cells do or do not undergo cell cycle entry, blast transformation and proliferation is readily ascertainable. A sample of cells including the cancerous B cells from a human patient, other mammalian host or from a cell line is cultured in vitro with a CLL cell proliferation-inducing (potentiating) amount of an immune response-enhancing agent and it is determined whether or not the cancerous B cells undergo blast transformation and proliferation. Exemplary procedures for such an assay are discussed hereinafter, and typically involve the uptake of a radiolabelled DNA precursor.

An increase in radiolabelled DNA precursor uptake of at least about two times that of uncontacted cells is taken as evidence of cell cycle entry, blast transformation and proliferation for in vitro studies. Furthermore, morphological blast transformation can be assessed on stained preparations under a microscope. For in vivo applications, peripheral blood smears, or lymphold tissue from patients with indolent B cell cancer typically exhibit few, if any, blasts. Thus, a microscopic examination of peripheral lymphocytes or involved lymphoid tissue subsequent to contacting with the immune response-enhancing agent that shows even as little as about one to about two percent blasts, and preferably more than about five percent blasts, indicates that cell cycle entry, blast transformation and proliferation have occurred.

The same amount of an immune response-enhancing agent, a CLL cell potentiating (proliferation-inducing) amount, is used in either of the above processes. For cells that do not proliferate and undergo cell cycle entry, blast transformation, the amount for use is determined from in vitro studies with CLL cells that do undergo blast transformation and proliferation. Loxoribine (7-allyl-8-oxoguanosine) used primarily herein is an excellent first choice compound for use. It is to be understood that different immune response-enhancing agents exhibit different potencies for mitogenesis or induction of proliferation and blast transformation. See, for example, the data of FIG. 6. Nevertheless, the appropriate concentration (CLL cell proliferation-inducing amount) to use is readily ascertainable by use of different concentrations to contact CLL cells. It is also to be understood that the immune response-enhancing agent used for determining whether cells undergo blast transformation and proliferation need not be the same material that is used to contact the cells in an above process, although that is preferred. Typical concentrations for such uses are about $10^{-4}$ to about $10^{-3}$ molar.

The aqueous medium employed in vitro studies is a typical medium used for culturing mammalian cells. The use of fetal calf serum (FCS) as part of that medium is helpful. However, it is especially preferred to use autologous plasma instead; i.e., plasma from the cancer cell donor. Each material is used at about 5 to about 15 volume percent of the medium, and more preferably at about 10 volume percent of the aqueous medium.

The biological culture conditions utilized are those normally used in mammalian cell culture. Thus, the temperature, atmosphere, osmolarity and pH value of the medium are those normally used in the culture of mammalian cells and are well known by skilled workers. Exemplary procedures are discussed hereinafter.

For in vivo contacting, the mammalian host's body fluids, e.g. blood, lymph and the like, provide the aqueous medium. The host mammal's body and body fluids also provide the biological culture conditions during the contact and maintenance steps.

Maintenance times for in vitro contacting are typically about 1 to about 29 days for the step using an immune response-enhancing agent, and as discussed below (about 6 to about 25 days) for the anti-cancer drug contacting and awaiting cell death. For in vivo contacting, contact times are a function of the mode of administration, and bodily degradation and excretion mechanisms. The pharmacokinetics for many anti-cancer drugs are well known.

Where, for example, an immune response-enhancing agent is provided in an oleagenous liquid diluent medium such as sesame oil, the half-life of a drug such as loxoribine is about 8–12 hours in humans. A typical regimen using a sesame oil diluent provides five bolus injections, at one per day over five days, with a second cycle beginning 16 to 23 days after the last injection. For aqueous intravenous administration and contacting, the half-life is shorter and a continuous or continual infusion over about five to about 14 days is contemplated, followed by a repeat of the administration about 23 to about 14 days after the last infusion.

Evidence of increased cancer cell death and thus the maintenance time for the contacted cells to die is typically about one to 30 days after contacting with the immune response-enhancing agent, and more usually about 6 to 25 days. The differential between live (or dead) contacted and non-contacted cells increases with time thereafter. Evidence for cell death is obtained by standard techniques such as FACS analysis or microscopic evaluation of stained or otherwise labeled cells.

Figure 2:
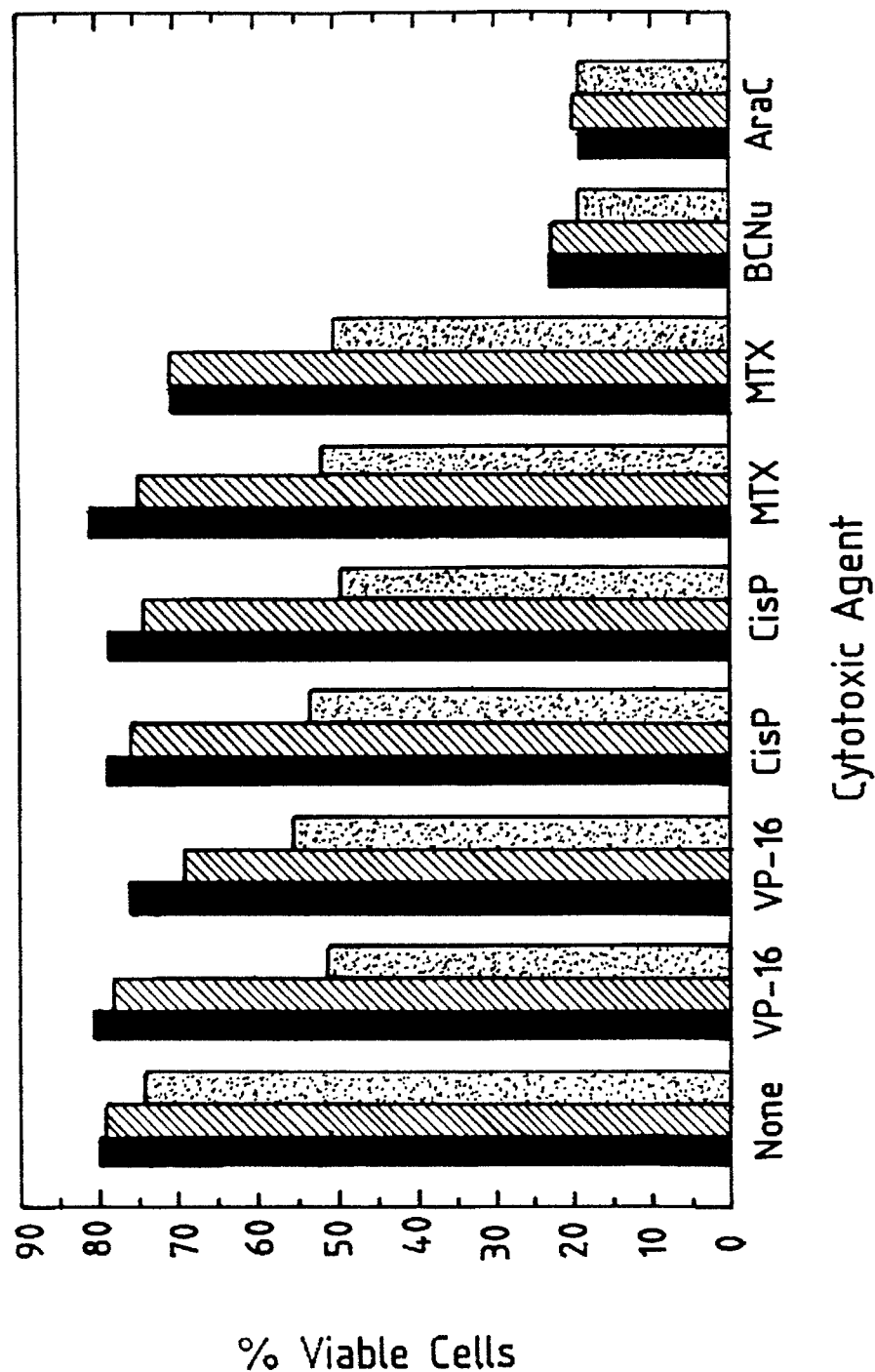
FIG. 2 illustrates the results of a two-stage assay performed essentially as described in FIG. 1 and Example 2 using peripheral CLL cells from another CLL patient, which cells do not undergo blast transformation and proliferation when contacted with loxoribine. The following anti-cancer drugs listed from left to right along the X-axis were maintained with either untreated or loxoribine-contacted (0.3 mM and 1.0 mM) cells for three days resulting in a total incubation period of five days: VP-16 (etoposide; 1 μg/ml and 10 μg/ml), Cis-P (cisplatin; $10^{-6}$ and $10^{-5}$M), MTX (methotrexate; $10^{-6}$ and $10^{-5}$M), BCNU (carmustine; $10^{-5}$M), and AraC (cytarabine; $10^{-5}$M). The data are plotted as described for FIG. 1.

The data of FIG. 1 illustrate the percentages of viable cells at day 3 of culture (one day post anti-cancer drug contact) for the non-proliferating cells, here CLL cells. As can be seen, the anti-cancer drug alone had a moderate to little cytotoxic effect at day 3 of culture. Similarly, contact with proliferation-inducing amounts of an immune response-enhancing agent, here loxoribine, had some cytotoxic effect at day 3; the anti-cancer drug+loxoribine contacting frequently reduced the number of viable cancer cells by about one-half to about two-thirds. FIG. 2 shows results for non-proliferating CLL cells from another patient.

The second-named process is similar to the before-described variant of the first process except that the contacted cells undergo blast transformation and proliferation in response to being contacted with the immune response-enhancing agent. The results shown in FIG. 3 were obtained using cells of a CLL patient that underwent cell cycle entry, blast transformation and proliferation when contacted with loxoribine that were then contacted with an anti-cancer drug.

It is preferred in both processes herein that the cancerous B cell contacting step using an immune response-enhancing agent be followed by a further contacting with an anti-cancer drug. Thus, the first contacting potentiates the cancerous B cells to the second contacting step, and makes that second contacting step more efficient in killing the cancerous B cells.

Anti-cancer drugs are typically not very effective against certain contemplated B cell cancers. This can be seen from the data of FIGS. 1–3. Thus, the cytotoxic amount of such drugs that is utilized herein is the usual amount of such drugs utilized for treating CLL as well as other cancerous conditions.

Some contemplated anti-cancer drugs such as chlorambucil and dexamethasone are utilized in treating B cell cancers such as CLL. However, as is shown in the data of FIGS. 1–3, a potentiation of the effect of those drugs is observed when the cancerous B cells are previously contacted with the immune response-enhancing agent as described herein.

Figure 3:
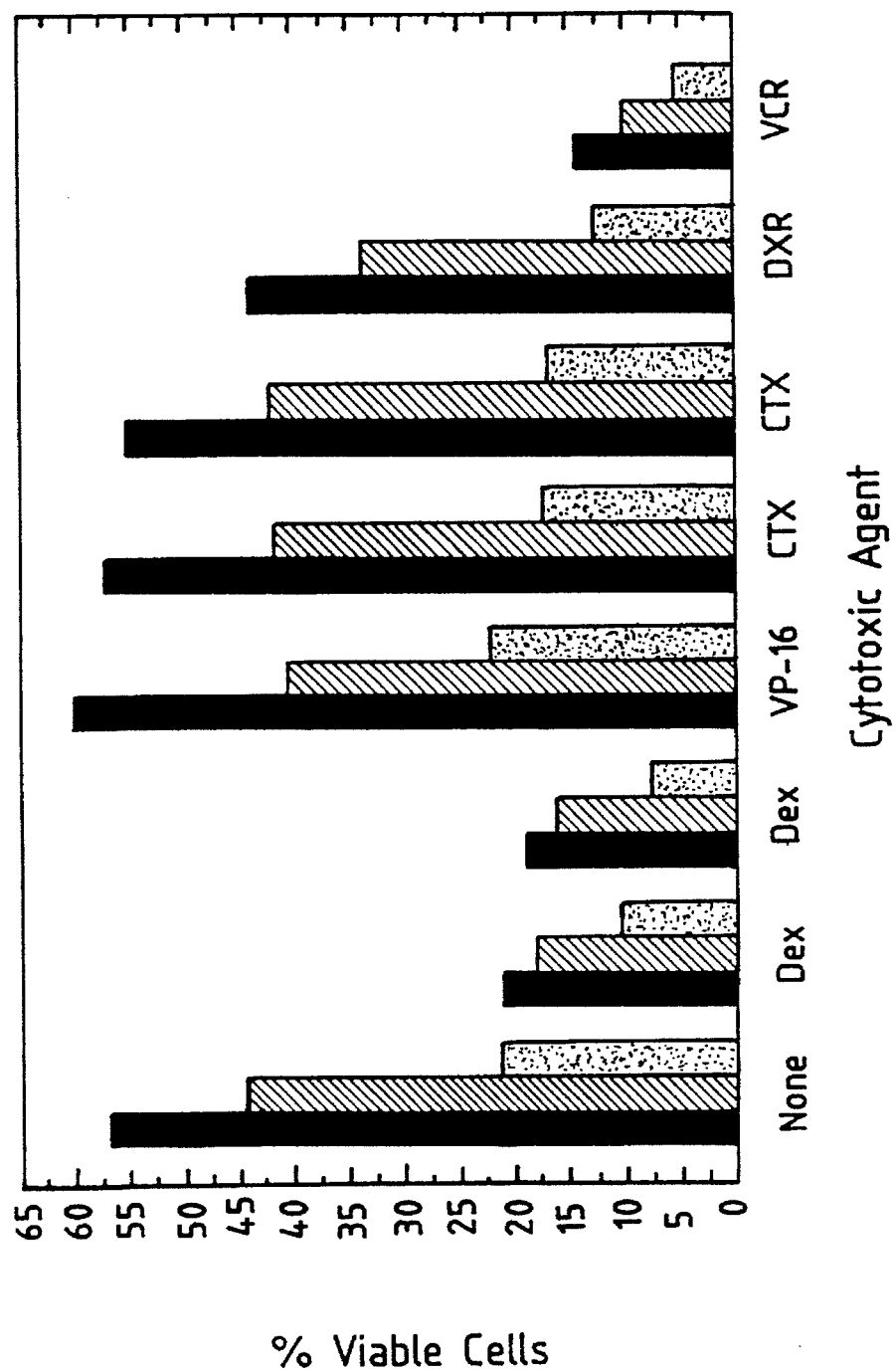
FIG. 3 illustrates the results of a two-stage assay in which a different CLL patient's peripheral CLL cells that do undergo blast transformation and proliferation when contacted with loxoribine were contacted with anti-cancer drugs for four days following loxoribine contacting as described in FIG. 1 and Example 2 for a total incubation period of six days. The data are plotted as described for FIG. 1. The anti-cancer drugs assayed and listed from left to right on the X-axis included DEX (dexamethasone; $2\times10^{-7}$M and $2\times10^{-6}$M), VP-16 (etoposide; 2 μg/ml), CTX (cytoxan; $2\times10^{-7}$M and $2\times10^{-6}$M), DXR (doxorubicin; $2\times10^{-7}$M) and VCR (vincristine; $10^{-6}$M).

The data of FIGS. 1–3 illustrate that not all anti-cancer drugs are equally useful in either process, nor is a particular anti-cancer drug that is effective with cells from one patient necessarily as effective with cells from another patient. For example, vincristine was not particularly effective alone when contacted with the patient cells shown in FIG. 1, but was quite effective alone when contacted with the patient cells shown in FIG. 3. Both cytotoxic effects of vincristine were potentiated by the prior contacting of those cancer cells with loxoribine.

The data of FIGS. 1–3 also show that a skilled worker can readily select an optimal anti-cancer drug for a particular patient by use of assays similar to those whose results are shown in those figures. Use of an appropriate anti-cancer drug can then be combined with contacting of the cancerous B cells with a CLL cell proliferation-inducing amount of an immune response-enhancing agent as is discussed herein to provide an optimal regimen for killing a particular patient's cancerous B cells.

In another aspect of either of the before-described processes, the cancerous B cells are contacted again with a CLL cell proliferation-inducing amount of an immune response-enhancing agent while those cells are in contact with the anti-cancer drug. It is believed that such further contacting provides further potentiation to the anti-cancer drug's effects.

Figure 5:
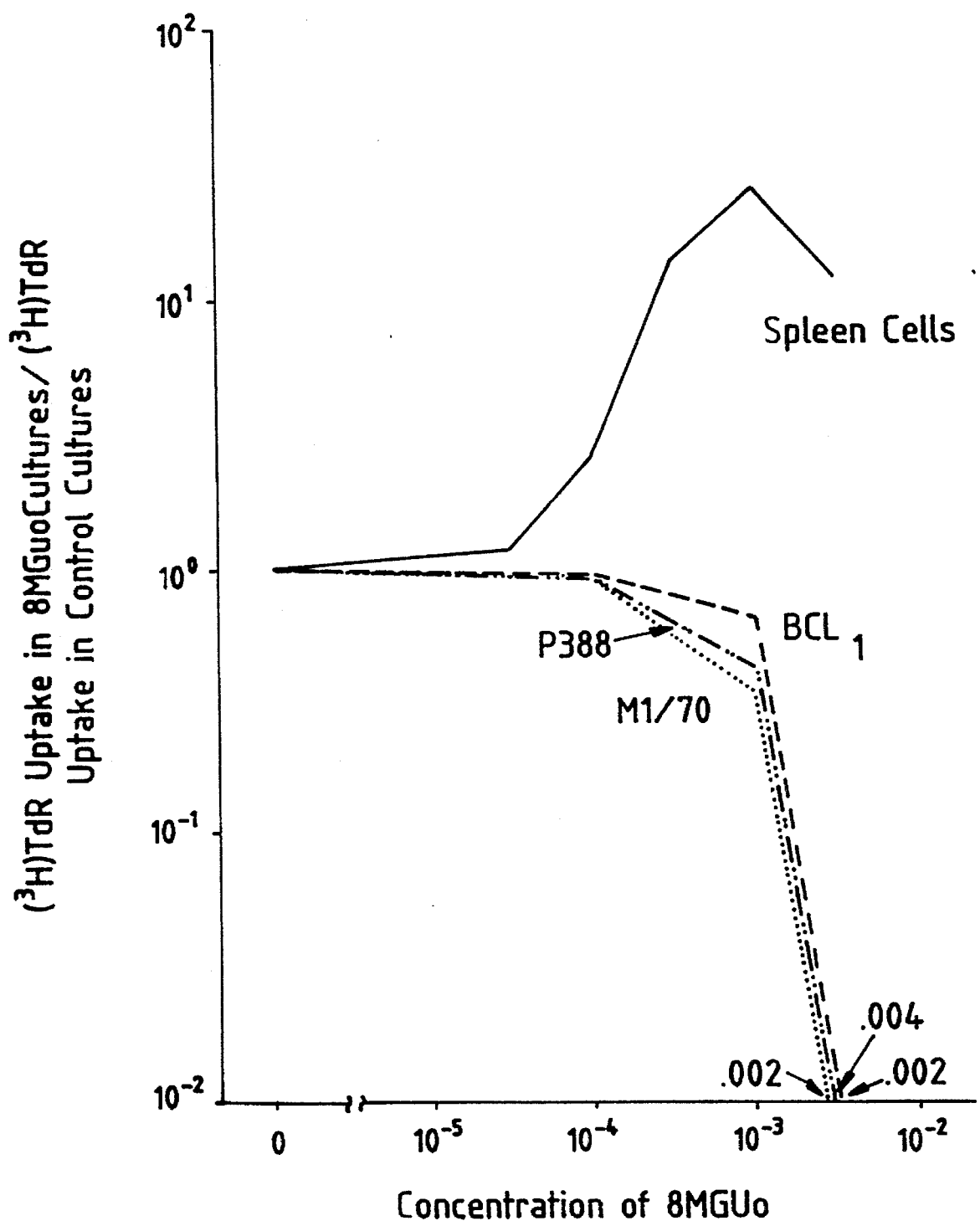
FIG. 5, which is also FIG. 27 of U.S. Pat. No. 4,539,205 and its subsequent patents and applications is a graph that illustrates the proliferation of normal mouse spleen cells, including B cells, upon contacting with the immune response-enhancing agent 8-mercaptoguanosine (8MGuo). Also shown are the cytotoxic results of contacting similar amounts of 8MGuo with cells of B cell cancer cell lines $BCL_1$ ($BCL_1 5B_1 b$, ATCC TIB 197) and M1/70 (M1/70.15.11.5HL, ATCC TIB 128), as well as the monocytic line P388 (obtained from the Cell Distribution Center of the Salk Institute for Biological Studies, La Jolla, Calif.). The ordinate is in units of ($^3$H)TdR uptake, whereas the abscissa shows the molar concentration of 8MGuo.

It is to be further understood that an immune response-enhancing agent used in an above process can induce a mitogenic, antigen-specific or other immune response to normal, non-cancerous, B cells as are discussed in the before-mentioned U.S. patents. Such responses are, however, benign, particularly as compared to the lethal, cancerous condition. The mitogenic effect of one immune response-enhancing agent, 8-mercaptoguanosine (8MGuo) on mouse spleen cells is shown in the graph of FIG. 5. Also shown in that graph is the cytotoxic effect of the same concentrations of 8MGuo on the P388, $BCL_1$ and M1/70 cancerous cell lines.

It is to be emphasized that although complete killing of contacted cancerous B cells is a desirable result, that result is not required. Any reduction in the number of cancerous B cells over an initial or control amount in an in vitro study as discussed herein can be used to evidence a desired effect and is advantageous to the patient. A reduction of at least 5 percent in the cancerous B cell count is a preferred minimum amount of killing, with increased percentages through complete elimination of the cancerous cells being the ultimate goal of treatment. However, it must be emphasized that even as little as one-half percent greater amount of cancer cell death, particularly where both an immune-enhancing and anti-cancer drug are used together, measured in vitro can be the difference in vivo between a partial and complete remission due to further augmentation of the killing effect by the patient's own immune defenses such as antibody or killer cell attacks on the cancer cells.

B. Anti-Cancer Druas

As noted before, embodiments of the invention contemplate chemotherapeutic methods for inhibiting the progression of malignancies such as leukemias, lymphomas and the like.

A cytotoxic agent, anti-cancer drug or anti-neoplastic agent for use in a present process can be any of a variety of compounds that are antimetabolites or that otherwise exhibit toxicity for dividing or resting cells. The clinical pharmacology of an anti-cancer drug for use in a present process can include a number of mechanisms of action.

Exemplary alkylating agents include cyclophosphamide (CTX; cytoxan), chlorambucil (CHL; leukeran), cisplatin (CisP; CDDP; platinol) busulfan (myleran), melphalan, carmustine (BCNU), streptozotocin, triethylenemelamine (TEM), mitomycin C, and the like alkylating agents.

Exemplary antimetabolites include methotrexate (MTX), etoposide (VP-16; vepesid), 6-mercaptopurine (6MP), 6-thioguanine (6TG), cytarabine (Ara-C), 5-fluorouracil (5FU), dacarbazine (DTIC), 2-chlorodeoxyadenosine (2-CdA), and the like antimetabolites.

Exemplary antibiotics include actinomycin D, doxorubicin (DXR; adriamycin), daunorubicin (daunomycin), bleomycin, mithramycin and the like antibiotics.

Exemplary alkaloids include vincristine (VCR), vinblastine, and the like.

Other anti-cancer agents include the cytostatic agents glucocorticoids such as dexamethasone (DEX; decadron) and corticosteroids such as prednisone, nucleotide enzyme inhibitors such as hydroxyurea, and the like diverse anti-cancer agents.

The synthesis and formulation of the above anti-cancer drugs is well known, is described in a variety of sources, and therefore will not be repeated here. Exemplary sources for synthesis and formulations of anti-cancer drugs include *Physician's Desk Reference*, Barnhart, eds., Medical Economics Company, Inc., Oradell, N.J., 1992, *Merck Index*, 11th Edition, Merck & Co., 1989.

It has also been found that contacting cancerous human B cells with a potentiating amount of an immune response-enhancing agent induces the contacted cells to express enhanced amounts of cell surface antigens in a dose-dependent manner. Included among those up-regulated antigens are the well-known antigens denominated CD-22, CD-23 (low affinity IgE Fc receptor), CD-25 (IL-2 receptor; p55, Tac), CD-38 and CD-54 (ICAM-1).

This antigen up-regulation permits use of anti-cancer or other cytotoxic agent conjugates for therapy. A contemplated conjugate is a single molecule composed of two portions. One portion binds to a before-discussed antigen. The second portion is a before-discussed anti-cancer agent or another cytotoxic agent such as ricin or diphtheria toxin and the truncated pseudomonas exotoxin known as PE40 that is linked to the first portion. PE40 contains domains II and III of the Pseudomonas exotoxin and has a molecular mass of about 40 kD, compared to the about 66 kD mass of the complete exotoxin.

Exemplary conjugates include IL-2-ricin, IL-2-daunorubicin or -doxorubicin conjugates. Antibodies to an above-noted antigen linked to an anti-cancer or other cytotoxic agent such as those noted herein can also be useful. Such antibodies were utilized in the fluorescence-activated cell sorter (FACS) assays that identified the up-regulated antigens. Further exemplary antibodies to CD23 are reported in Flores-Romo et al., *Science*, 261:1038–1041 (1993). Waldman, Science, 252:1657–1662 (1991) reports use of antibodies to ICAM-1 and to the IL-2 receptor (anti-Tac), as well as successful treatment of patients having HTLV-1-associated T cell diseases with the anti-Tac antibodies, and also positive results with a genetically engineered anti-Tac (Fv)-PE40 toxin conjugate. Further exemplary anti-CD-25 antibodies are available from the American Type Culture Collection (ATCC), 12301 Parklawn Drive, Rockville, Md. 20852 as HB 8555 and HB 8784, as are anti-CD-38 antibodies (OKT10, CRL 8022). Exemplary procedures for linking anti-cancer agents to monoclonal antibodies can be found in Mueller et al., *Antibody Immnunoconjugates Radiopharmaceuticals*, 4(2):99–106 (1991) (morpholino-doxorubicin); Elias et al., *Cancer Res.*, 50:4154–4159 (1991) (methotrexate); Mueller et al., *Broconjugate chem.*, 1(5): 325–330 (1990) (morpholino-doxorubicin); and Reisfeld et al., *Immunol. Allergy Clin. N. Amer.*, 11(2):341–358 (1991) (several drugs), and the citations therein.

The use of the above anti-cancer drugs and conjugates in chemotherapeutic regimens is well known in the cancer therapy arts. Their use herein falls under the same considerations for monitoring tolerance and effectiveness, using similar administration routes and dosages, with some adjustments. For example, the actual dosages of the anti-cancer drugs can vary depending upon the host mammal's cultured cell response to potentiation by the immune response-enhancing agent. Generally, the dosage is reduced compared to the amount used in the absence of immune response-enhancing agent, although usual dosages of anti-cancer drug are also used.

Typical dosages of effective anti-cancer drugs are in the ranges recommended by the manufacturer, and where indicated by in vitro responses, can be reduced by up to about one order of magnitude concentration or amount. Thus, the actual dosage depends upon the judgment of the treating physician for in vivo use, the condition of the patient, and the effectiveness of the therapeutic method based on the in vitro responsiveness of the primary cultured cancerous B cells.

Further information such as treatment regimens, structures, toxicity, and the like about the before-mentioned anti-cancer drugs can be found in *The Pharmaceutical Basis of Therapeutics*, Goodman and Gilman eds., 6th ed., The Macmillan Co., New York, N.Y. (1980), and in Goth, A., *Medical pharmacology*, 9th ed., The C.V. Mosby Co., St. Louis, Mo., (1978), and in the citations therein. Specific further information concerning many of the above anti-cancer drugs can also be found in the *Physicians' Desk Reference*, 27–39th editions, Medical Economics Company, Oradell, N.J., (1973–1985). Still further information concerning useful anti-cancer drugs can be found in *Reminaton's Pharmaceutical Sciences*, Osol ed., 16th ed., Mack Publishing Co., Easton, Pa. (1980). Dosages of anti-cancer drugs conjugated to antibodies or ligands for the before-mentioned up-regulated surface antigens are typically considerably less than standard dosages for such drugs administered systemically in accordance with current practice.

C. Immune Response-Enhancing Agents

An immune response-enhancing agent useful herein is preferably a compound disclosed in U.S. Pat. Nos. 4,653, 992, 4,746,651, 5,011,828, 5,093,318, 4,880,784, and 5,166, 141, whose disclosures are incorporated herein by reference.

The immune response-enhancing agents are members of one of two classes of aldoglycosides, the (1) 8-substituted- and 7,8-disubstituted-9-aldoglycosidylguanines, and (2) the 6-substituted-8-aldoglycosidylisoxanthopterins. These compounds correspond generally in structure to formulas I and II, respectively hereinbelow,

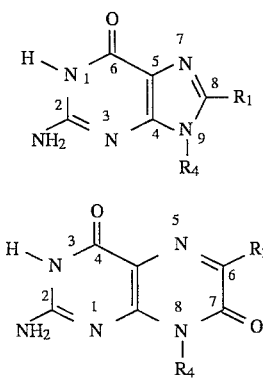

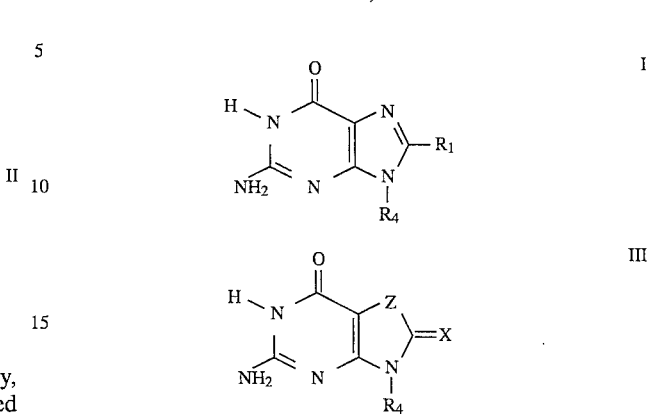

wherein $R_1$ and $R_3$ are 8- and 6-substituents, respectively, and $R_4$ is the aldoglycoside, all of which are discussed in detail hereinafter.

When $R_1$ is hydroxy or mercapto, a compound of formula I can tautomerize to place the endocyclic double bond that was at the 7,8-position at a position exocyclic to the ring, and provide a further useful valance for substitution on the nitrogen at the 7-position. The tautomerized hydroxy and mercapto groups are referred to as oxo (O=) and thioxo (S=), respectively. The oxo and thioxo guanine derivatives are thus viewed as species of the compounds of formula I, above.

Several tautomerized 7-substituted-8-oxo- and 7-substituted-8-thioxo-guanine derivatives are useful herein, as are similar 7-oxa- and 7-thia-analogs of 8-oxo- or 8-thioxo derivatives of guanine that are believed to exist substantially only in the 8-oxo and 8-thioxo forms. The structures of these compounds correspond to formula III, below

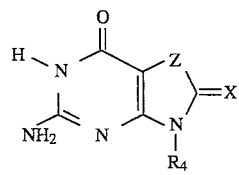

wherein Z is oxygen (O), sulfur (S) or substituted nitrogen (N—$R_2$); X is oxygen (O) or sulfur (S); $R_2$ as described hereinafter; and $R_4$ is the aldoglycoside that is also described hereinafter. It is noted that an isoxanthopterin derivative of formula II can also tautomerize when $R_3$ is hydroxy or mercapto, and form the corresponding oxo- and thioxo-substituted derivatives, respectively.

1. Guanine Derivatives

The guanine derivatives useful herein are readily prepared by procedures published in the chemical literature, or by procedures analogous thereto. Syntheses of 8-substituted guanine derivatives typically begin with the 9-1'-aldoglycoside bond already formed. The general mode of synthesis of such 9-(1'-beta-D-aldoglycosidyl)-guanines as are useful is known. Exemplary syntheses are illustrated in Holmes and Robins, *J. Am. Chem. Soc.*, 86:1242–1243 (1964); Ibid., 87:1772–1776 (1965); Long et al., *J. Org. Chem.*, 32:2751–2756 (1967); Gerster et al., *J. Org. Chem.* 33:1070–1073 (1968); Rizkalla et al., *Biochim. Biophys. Acta*, 195:285–293 (1969); Miller et al., *Biochemistry*, 12:5310–5319 (1973); U.S. Pat. Nos. 5,011,828 and 5,093,318, the latter two teachings being incorporated by reference. Exemplary guanine derivatives have a structure that conforms to formulas I and III, below.

The $R_1$ group or radical of the compounds of formula I contains up to about 20 atoms, and more preferably, up to about 15 atoms. Most preferably, $R_1$ contains 1 to about 7 atoms. $R_4$ is the aldoglycosidyl radical that is discussed hereinafter.

One convenient way of characterizing useful $R_1$ groups (8-substituents) of the guanine derivative of formula I is by their electron withdrawing inductive effects relative to hydrogen. Hammett substituent sigma constants (sigma constants) calculated for ionization of meta-substituted benzoic acids are useful in predicting relative inductive effects, and are well known to those familiar with physical organic chemistry. See, for example, Hine, *Physical Organic Chemistry*, McGraw-Hill Book Company, New York, pp. 85–88 (1962).

Those substituents that have a greater inductive electron withdrawing effect than hydrogen have positive sigma constant values. Those substituents that exhibit less of an inductive electron withdrawing effect than hydrogen; i.e., electron donors, have negative sigma constant values.

Preferred $R_1$ groups have an inductive electron withdrawing effect greater than that of hydrogen. Illustrative of such 8-substituents are halo, hydroxy, mercapto, $C_1$–$C_6$ alkyloylthio ($C_1$–$C_6$ acylthio), $C_1$–$C_6$ alkyl sulfides also known as $C_1$–$C_6$ thioalkoxy radicals or $C_1$–$C_6$ alkylthio radicals, nitro, cyano, $C_1$–$C_6$ alkoxy, halomethyl such as bromomethyl or chloromethyl, $C_1$–$C_6$ alkanoyl ($C_1$–$C_6$ acyl), trifluoromethyl, $C_1$–$C_6$ alkanamido ($C_1$–$C_6$ acylamido), $C_1$–$C_6$ alkyl sulfonyl, sulfonamide and methyleneoxy $C_1$–$C_6$ alkyl ethers such as methyleneoxyethyl (—$CH_2$—O—$CH_2CH_3$). Hydroxy (OH) and mercapto (SH) are particularly preferred $R_1$ groups.

With reference to Hammett substituent sigma constants for meta benzoic acid substituents, the preferred 8-substituents have positive values. More preferably, the 8-substituents have sigma constants of about 0.1 to about 0.7. The most preferred 8-substituents have sigma constants of about 0.1 to about 0.4. It is noted that sigma constants have not been measured for all of the preferred 8-substituents. However, the absence of such a measurement for a 8-substituent is not an indication that the 8-substituent is not among the preferred class of substituents.

Where Z is N—$R_2$, the $R_2$ group of the guanine derivative of formula III has a length up to about that of an n-decyl ($C_{10}$) group and is more preferably $C_1$–$C_6$ alkyl (most preferably $C_3$–$C_6$ alkyl), $C_3$–$C_{10}$ beta-alkenyl, halo $C_1$–$C_{10}$ alkyl or benzyl. Also contemplated are radicals that include nitrobenzyl, $C_1$–$C_6$ alkoxybenzyl, polyhalo $C_1$–$C_{10}$ alkyl, phenyl-substituted $C_3$–$C_6$ beta-alkenyl, hydroxy $C_1$–$C_{10}$ alkyl, $C_1$–$C_{10}$ alkanoyl, polyhydroxy $C_1$–$C_{10}$ alkyl, $C_1$–$C_6$ alkoxy $C_1$–$C_6$ alkylenecarbonyl, $C_1$–$C_6$ alkylene $C_1$–$C_6$ alkylcarboxylate, and $C_1$–$C_6$ alkyl carboxamido in which the carboxamido group has the formula $CONR_9R_{10}$ wherein $R_9$ and $R_{10}$ are the same or different and are selected from the group consisting of hydrogen and $C_1$–$C_6$ alkyl, or $NR_9R_{10}$ together form a heterocyclic ring containing five or six atoms in the ring. It is particularly preferred that X be oxygen. A particularly preferred compound of formula III corresponds to the formula

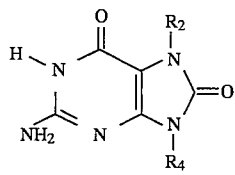

The guanine ring is itself free from electrically (ionically) charged functionality in water at pH 7.2–7.4 other than that charge that is provided by hydrolysis reactions of water with the weakly acidic amine substituents of the guanine ring. Thus, except where tautomerization can occur through an 8-hydroxy or 8-mercapto group, the nitrogen atom at the 7-position is unsubstituted since a substitution on that nitrogen would form a quaternary atom having a permanent positive charge. In addition, the useful guanine derivatives are free from phosphate groups that can bear an electric charge at physiological pH values.

7-Oxa- and 7-aza-guanosines of formula III are described in U.S. Pat. Nos. 4,880,784 and 5,166,141, whose disclosures are incorporated herein by reference.

2. Isoxanthopterin-8-Aldoqlycosides

2-Amino-4-hydroxypteridine and its derivatives are known in the art as pterin and its derivatives, respectively. Prototropically active pterins are usually represented in their most favored tautomeric formula as 2-aminopterin-4-one and its derivatives, Pfleiderer, Chapter 2.16 in *Comprehensive Heterocyclic Chemistry*, Vol. 3, Part 2B, Katritzky and Rees eds., Pergamon Press, New York (1984) pages 63–327.

2-Amino-4,7-dihydroxypteridine and its tautomer 2-aminopterin-4,7-dione are known as isoxanthopterin. A more precise chemical name for isoxanthopterin is 2-amino-3,4,7,8-tetrahydro-4,7-dioxopteridine. The compounds useful herein will generally be referred to as isoxanthopterin and its derivatives. These useful isoxanthopterin derivatives all possess an aldoglycoside (sugar aldehyde) as a substituent at the 8-position of the pteridine ring system, and can also include a substituent other than hydrogen at the 6-position.

Isoxanthopterin and 6-substituted isoxanthopterins for preparation of the isoxanthopterin derivatives useful herein are themselves readily prepared by known reactions. In one reaction scheme, a 2,5,6-triamino-4-hydroxypyrimidine is reacted with an alpha-keto acid in which a substituent beta to the carboxy group forms the $R_3$ group in the structural formulas herein. See, Hurst, *An Introduction to the Chemistry and Biochemistry of Pyrimidines, Purines and Pteridines*, John Wiley & Sons, New York, pages 86–103 (1980), and the citations therein. In another reaction scheme, the above pyrimidine is reacted with a di-lower alkyl ester of an acetylene dicarboxylic acid to form a lower alkyl carboxylic acid at the 6-position and lower alkyl esters thereof. Iwanami, *Bull. Chem. Soc. Japan*, 44:1314 (1971). Still further compounds and reaction schemes are discussed in Pfleiderer, Chapter 2.16 of *Comprehensive Heterocyclic Chemistry*, supra.

The isoxanthopterin 8-aldoglycoside derivatives useful herein are preferably prepared from isoxanthopterin or a 6-substituted isoxanthopterin derivative to which the aldoglycosidic group is thereafter added by the method of Pfleiderer as described in U.S. Pat. No. 3,798,210, whose disclosures are incorporated herein by reference. Other methods of preparation such as the cyclization of a 2-amino-3,4-dihydro-5-nitro-4-oxo-6-aminoglysidylpyridmidine described by Lohrmann and Forrest, *J. Chem, Soc.*, 460–465 (1965) are also useful.

Briefly, in accordance with the Pfleiderer technique, a suitably substituted isoxanthopterin is O-metalized at the 7-position with a quadrivalent metal of the fourth main group and third to fifth period of the periodic system. The O-metalized compound so prepared is reacted with an aldoglycoside whose 1'-position hydroxyl group is itself derivatized as a reactive ester such as an ester of a lower carboxylic acid ester like acetic acid, or as an ether such as a lower alkyl ether like a methyl ether. The 1'-position hydroxyl can also be replaced by a halo group such as bromide as taught by Pfleiderer and his co-workers in *Chem. Ber.*, 106:317–331 (1973); *Chem. Ber.*, 106:1952–1975 (1973); and *Chem. Ber.*, 107:339–361 (1974).

Quadrivalent germanium, tin and especially silicon are preferred O-metalizing agents. The particularly preferred O-metalizing agent is hexamethyldisilazane.

A strong acid catalyst such as an inorganic acid like sulfuric acid is preferably used with an O-metalizing agent such as hexamethyldisilazane. The hexamethyldisilazane is preferably utilized in excess, in the absence of water, and preferably in the presence of nitrogen or argon rather than air.

The 7-O-metalized isoxanthopterin is thereafter typically collected and reacted in an inert solvent such as dry benzene with the aldoglycoside whose hydroxyl groups other than that of the 1'-position are protected, as by benzoyl or acetyl groups. The 1'-position of the chosen aldoglycoside is derivatized as before discussed.

The glycosidation reaction is preferably carried out in the presence of a mercuric salt such as a mercuric halide, or mixture of mercuric halides where an aldoglycosidyl 1'-ether or 1'-ester is used. An elevated temperature such as that of refluxing benzene at one atmosphere of pressure is used for the aldoglycosylation reaction (condensation of sugar and isoxanthopterin).

The mercury salt, where used, is filtered from the reaction medium once the reaction is over, and the isoxanthopterin-S-(hydroxy protected aldoglycoside) derivative is recovered as by column chromatography. The hydroxy protecting groups, e.g., benzoyl or acetyl, are thereafter removed by standard procedures such as reaction in sodium methoxidemethanol, followed by neutralization. The desired isoxanthopterin-8-(1'-aldoglycoside) derivative is thereafter collected and purified, as by crystallization.

Useful isoxanthoperin derivatives have a structure that corresponds to formula II, before,

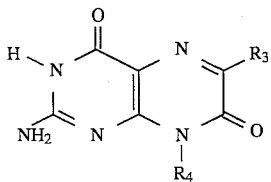

wherein

R$_3$ is a radical selected from the group consisting of hydrogen, $C_1$–$C_6$ alkyl, hydroxy $C_1$–$C_6$ alkyl, polyhydroxy $C_1$–$C_6$ alkyl, phenyl, phenyl-$C_1$–$C_6$ alkylene, $C_1$–$C_6$ alkyl phenyl, $C_1$–$C_6$ $_6$ alkoxy phenyl, halophenyl, trifluoromethylphenyl, hydroxy, oxo (O=), $C_1$–$C_6$ alkoxy, phenyl-$C_1$–$C_6$ alkoxy, halo, mercapto, thioxo (S=), $C_1$–$C_6$ alkylthio, phenyl-$C_1$–$C_6$ alkylthio, $C_1$–$C_6$ alkanoyl ($C_1$–$C_6$ acyl), $C_1$–$C_6$ alkoxy carbonyl, $C_1$–$C_6$ alkylene $C_1$–$C_6$ alkylcarboxylate, $C_1$–$C_6$ alkoxy $C_1$–$C_6$ alkyl carbonyl, and $C_1$–$C_6$ alkyl carboxamido in which the carboxamido group has the formula $CONR_9R_{10}$ wherein $R_9$ and $R_{10}$ are the same or different and are selected from the group consisting of hydrogen and $C_1$–$C_6$ alkyl or $NR_9R_{10}$ together form a heterocyclic ring containing five or six atoms in the ring;

R$_4$ is an aldoglycoside radical as described hereinafter that is selected from the group consisting of 1'-aldopentosidyl, 1'-aldohexosidyl, monodeoxygenated 1'-aldopentosidyl and mono-deoxygenated 1'-aldohexosidyl radicals bonded beta to the 8 position of an isoxanthopterin.

In particularly preferred practice, R$_3$ is hydrogen, hydroxy, $C_1$–$C_6$ alkyl, $C_1$–$C_6$ alkoxy carbonyl, e.g., ethoxycarbonyl or methoxycarbonyl, and polyhydroxy $C_1$–$C_6$ alkyl.

Tautomers of the isoxanthopterin derivatives are also contemplated.

3. Exemplary R$_1$, R$_2$ and R$_3$ Radicals

Reference has been made hereinbefore to R$_1$, R$_2$ and R$_3$ groups, radicals (moieties) of an immune response-enhancing agent. Examples of those previously mentioned groups and radicals are provided hereinbelow as those radicals are applicable to the compounds of formulas I, II and III discussed hereinbefore. Consequently, where a group or radical can be an R$_1$ and an R$_3$ group or radical, that moiety can have up to about 20 atoms as an R$_1$, whereas a greater number of atoms is allowed for an R$_2$ or R$_3$ group or radical. $C_1$–$C_{10}$ groups and radicals denote that they possess 1 to about 10 carbon atoms, and more preferably 1 to about 6 carbon atoms ($C_1$–$C_6$), and most preferably about 3 to about 6 carbon atoms.

$C_1$–$C_6$ alkyl radicals include straight chain, branched chain and cyclic substituents. Exemplary alkyl groups, methyl, ethyl, propyl, iso-propyl, n-butyl, sec-butyl, t-butyl, n-pentyl, 2-methyl-3-butyl, 1-methylbutyl, 2-methylbutyl, neo-pentyl, n-hexyl, 1-methylpentyl, 3-methylpentyl, 1-ethylbutyl, 2-ethylbutyl, 2-hexyl, 3-hexyl, cyclopentyl, cyclohexyl, nonyl, octyl, decyl, and the like.

Hydroxy $C_1$–$C_{10}$ alkyl radicals include hydroxy methyl, 2-hydroxyethyl, 2-hydroxypropyl, 3-hydroxypropyl, 3-hydroxy-2-butyl, 3-hydroxy-2,2 -dimethylpropyl, 6-hydroxyhexyl and the like.

Polyhydroxy $C_1$–$C_{10}$ alkyl radicals include 1,2-dihydroxyethyl, 1,2,3-trihydroxypropyl, 2,3-dihydroxypropyl, 3,4-dihydroxybutyl, 8,9-dihydroxynonyl and the like. Those skilled in the art will understand that the contemplated polyols contain no more than one hydroxyl group on each carbon atom of the lower alkyl group.

Phenyl-$C_1$–$C_6$ alkylene radicals include phenyl-substituted $C_1$–$C_6$ alkylene radicals listed above, wherein the alkylene portion of the radical is bonded to the 6-position of the isoxanthopterin derivative. Exemplary radicals include benzyl, phenethyl, 2-phenylpropyl, 2-phenyl-3-methylpentyl and the like.

$C_1$–$C_6$ alkylphenyl radicals are the above-described lower alkyl radicals substituted on a phenyl radical that is itself bonded to the 6-position of an isoxanthopterin 8-aldoglycoside. Exemplary of such $C_1$–$C_6$ alkylphenyl radicals are o-xylyl, p-(2-hexyl)phenyl, m-(iso-propyl)phenyl, and the like. Trifluoromethylphenyl substituted ortho-, meta- or para- to the position of binding to the 6-position of the isoxanthopterin constitute a sub-class of lower alkylphenyl radicals.

$C_1$–$C_6$ alkoxyphenyl radicals are $C_1$–$C_6$ alkyl ethers of ortho-, meta- or para-isoxanthopterin substituted phenols, wherein the $C_1$–$C_6$ alkyl group is as described before. Exemplary $C_1$–$C_6$ alkoxy phenyl radicals include o-methoxyphenyl, m-sec-butoxyphenyl, and p-(2-ethylbutoxy)phenyl.

Halophenyl radicals utilize halogen-substituted phenyl radicals in which the halogen is preferably fluoro, chloro and bromo, and also include iodo. Exemplary radicals include o-chlorophenyl, p-fluorophenyl and m-bromophenyl.

Hydroxy and mercapto radicals can also be present as oxo and thioxo radicals, respectively, due to their tautomer formation, as already noted.

$C_1$–$C_6$ alkoxy radicals can be viewed as ethers formed from an 8-hydroxy guanine or a 6-hydroxy isoxanthopterin and a before-described $C_1$–$C_6$ alkyl group. Exemplary radicals include methoxy, ethoxy, propoxy, iso-propoxy, n-butoxy, and the like. Phenyl-$C_1$–$C_6$ alkoxy radicals can similarly be viewed as ethers formed from a 6-hydroxy isoxanthopterin and a before-described phenyl-$C_1$–$C_6$ alkyl radical. Exemplary of these materials are benzyloxy, 2-phenylethoxy, 2-phenylpropoxy and the like.

Halo radicals preferably include chloro, bromo, as well as fluoro and iodo. Halo $C_1$–$C_6$ alkyl groups are groups that contain one halogen atom substituted on an alkyl chain of 1 to about 10 carbons. A polyhalo $C_1$–$C_{10}$ alkyl group contains two or more halogen substituents on the alkyl group. Exemplary groups include 2-chloroethyl, 9,10-dibromodecyl, trifluoromethyl, perfluoroethyl ($C_2F_5$) 3-bromopropyl and the like.

$C_1$–$C_6$ alkylthio and phenyl-$C_1$–$C_6$ alkylthio radicals are sulfide ethers and are thus analogous to the oxygen ethers described above, as $C_1$–$C_6$ alkoxy and phenyl-$C_1$–$C_6$ alkoxy radicals, respectively.

A carboxyl radical is a carboxylic acid (—$CO_2H$) bonded to the 8- or 6-position of the guanine derivative or isoxanthopterin 8-aldoglycoside, respectively, and is not itself a contemplated substituent group as it provides a negative charge to the molecule. However, a contemplated substituent includes a $C_1$–$C_6$ alkoxy carbonyl radical that can be viewed as an ester of a carboxyl formed with a lower $C_1$–$C_6$ alcohol where the $C_1$–$C_6$ alkyl portion of the alcohol is a $C_1$–$C_6$ alkyl radical as before-described. Exemplary esters are ethyl, methyl, t-butyl, neo-pentyl carboxylates, and the like. These esters can also be named ethoxycarbonyl, methoxycarbonyl, t-butoxycarbonyl and neo-pentoxycarbonyl, respectively.

$C_1$–$C_6$ alkylenecarboxyl radicals are the before-described $C_1$–$C_6$ alkyl radicals that further include a carboxyl group. These groups also possess a negative ionic charge at pH 7.2–7.4 are also not contemplated substituents. However, a contemplated substituent includes a $C_1$–$C_6$ alkoxy $C_1$–$C_6$ alkylenecarbonyl radical that can be viewed as an ester of a $C_1$–$C_6$ alkylenecarboxyl radical with a $C_1$–$C_6$ alkyl alcohol, which is as described immediately above. Exemplary $C_1$–$C_6$ alkyl carboxyl radicals include carboxymethyl, 2-carboxyethyl, 2-carboxypentyl, 8-carboxyoctyl, and the like. Exemplary $C_1$–$C_6$ alkoxy $C_1$–$C_6$ alkylenecarbonyl radicals include isopropyl, 4-butyanoate, hexyl 4-methyl-pentanoate, and the like.

$C_3$–$C_6$ beta-alkenyl radicals, as can be the $R_2$ portion of a compound of formula III, contain an ethylenic double bond beta to the 7-nitrogen atom of the compound of that formula. Exemplary radicals include allyl, 3-but-1-enyl, 2-pentenyl, 3-methyl-2-pentenyl and the like. The cinnamyl radical is an example of a phenyl-substituted $C_1$–$C_6$ beta-alkenyl radical.

Mono- and disubstituted $C_1$–$C_6$ alkyl amides can be viewed as being formed from a carboxyl group and a mono-$C_1$–$C_6$ alkyl amine or di-$C_1$–$C_6$ alkyl amine, respectively, where the $C_1$–$C_6$ alkyl radicals are as before described. Exemplary of such amines are methylamine, propyl-amine, sec-butylamine, hexylamine, dimethylamine, methylethylamine, butylhexylamine and the like. Amides of cyclic secondary amines having five or six atoms in the ring can be viewed as being formed from a carboxyl group and a secondary amine such as pyrrolidine, morpholine, piperidine, pyrrole and 4-methylpiperazine. Unsubstituted amides are formed from ammonia as the amine.

$C_1$–$C_6$ alkylenecarboxamido radicals can be viewed as being formed from a $C_1$–$C_6$ alkylenecarboxyl group and an amine. The carboxamido group has the formula $CONR_9R_{10}$ wherein $R_9$ and $R_{10}$ are the same or different and are selected from the group consisting of hydrogen and $C_1$–$C_6$ alkyl. Alternatively, $NR_9R_{10}$ together can form a heterocyclic ring having five or six atoms in the ring. Exemplary useful amines are as discussed above.

$C_1$–$C_6$ alkanoyl radical substituents, also known as $C_1$–$C_6$ acyl radicals, contain a carbonyl group bonded directly to the 8-position of the guanine, the 6-position of the isoxanthopterin ring or the 7-position nitrogen atom of a guanine derivative of formula III in which $R_2$ is the $C_1$–$C_6$ alkanoyl radical, thereby making the compounds ketones, an aldehyde or an amide, as is appropriate. Exemplary $C_1$–$C_6$ alkanoyl groups include formyl, acetyl, propionyl, 2-methylpropionyl, butyryl, 3-methylvaleryl, cyclohexanecarbonyl, octanoyl and the like. The acyl carbon of the radical is considered a part of the $C_1$–$C_{10}$ alkanoyl or acyl group.

A $C_1$–$C_6$ alkylene $C_1$–$C_6$ alkylcarboxylate radical can be viewed as an ester of a substituent hydroxy $C_1$–$C_6$ alkyl radical and a $C_1$–$C_6$ alkyl carboxylic acid. Exemplary hydroxy $C_1$–$C_6$ alkyl substituents have been discussed previously, as have the $C_1$–$C_{10}$ alkanoyl (lower acyl) portions of $C_1$–$C_{10}$ alkyl carboxylic acids that can be present in such esters.

$C_1$–$C_6$ alkyloylthio or $C_1$–$C_6$ acylthio radicals can be viewed as thioesters formed from an appropriate 6- or 8-mercapto substituent of an isoxanthopterin or guanine derivative, respectively, and a $C_1$–$C_6$ alkyl carboxylic acid. Exemplary of such radicals are thioacetyl, thiopropionyl, thiohexanoyl and the like. A $C_1$–$C_6$ alkanamido ($C_1$–$C_6$ acylamide) radical is an amide that can be viewed as being formed from an 8-amino guanine derivative and a $C_1$–$C_6$ alkylcarboxylic acid. Exemplary of such radicals are formamido, acetamide, valaramido and the like. Thus, 8-acylamido guanine derivatives are useful while the corresponding amines are not.

$C_1$–$C_6$ alkyl sulfonyl radicals contain an —$SO_2$— group (sulfone) bonded to the 8-position of a guanine derivative and also to a $C_1$–$C_6$ alkyl group, as described hereinbefore.

The radical chain lengths are measured along the longest linear carbon chain in the substituent. Such lengths can be readily determined by using published bond angles, bond lengths and atomic radii, as needed, to draw and measure a staggered chain, or by building models using commercially available kits whose bond angles, lengths and atomic radii are in accord with accepted, published values. Radical lengths can also be determined somewhat less exactly by assuming unsaturated bonds to have the same length as saturated bonds and that bond angles for unsaturated bonds are the same as those for saturated bonds, although the above-mentioned modes of measurement are preferred. The lengths are determined as the longest length for the radical, including any heteroatom, such as oxygen, chlorine, or nitrogen.

The guanines and isoxanthopterin 8-aldoglycosides are weak acids, and as such can form base addition salts. Such salts are useful in providing storage stability and do not provide an added electric charge to a useful guanine derivative in situ because of the large buffering effect provided by the host's blood and lymph systems or the buffer of a culture medium.

Pharmaceutically acceptable, non-toxic base addition salts of guanine or isoxanthopterin derivatives are useful herein, and can be formed by treatment of the immune response-enhancing agent with an appropriate base, in a suitable solvent such as water or a lower alkyl alcohol such as methanol or ethanol. Exemplary inorganic bases include sodium, potassium, calcium and ammonium hydroxide, and the like bases. Exemplary organic bases include tris-(hydroxymethyl)-aminomethane (TRIS), 4-(2-hydroxyethyl)-1-piperazine-ethanesulfonic acid (HEPES) and the like bases. Conversely, the base addition salt form can be converted to the free guanosine or isoxanthopterin form by treatment with acid.

4. Aldoglycosides

The 8-aldoglycoside portion ($R_4$) of the useful guanine and isoxanthopterin derivatives are cyclic, contain 5 or 6 carbon atoms, and are selected from the group consisting of 1'-aldopentosidyl, 1'-aldohexosidyl, mono-deoxygenated 1'-aldopentosidyl, and mono-deoxygenated-1' -aldohexosidyl radicals. The useful aldoglycosides are bonded to the 9- or 8-position of the guanine or isoxanthopterin derivative, respectively. The aldoglycosides are free from electric charge and are therefore free from carboxy, phosphate and quaternary ammonium substituents.

Exemplary 1'-aldopentosidyl radicals are the 1'-radicals of ribose, arabinose, lyxose and xylose that are named 1'-ribofuranosidyl, 1'-arabinofuranosidyl, 1'-lyxofuranosidyl, and 1'-xylofuranosidyl radicals, respectively. Exemplary 1'-aldohexosidyl radicals are the 1'-radicals of glucose, galactose, mannose, gulose, allose, altrose, and rhamnose that are named 1'-glucopyranosidyl, 1'-galactopyranosidyl, 1'-mannopyranosidyl 1'-gulopyranosidyl, 1'-allopyranosidyl, 1'-altropyranosidyl, 1'-rhamnopyranosidyl, radicals, respectively. An exemplary mono-deoxygenated 1'-aldopentosidyl radical is that of deoxyribose that is named the 1'-(2'-deoxy)-ribofuranosidyl radical. An exemplary mono-deoxygenated 1'-aldohexosidyl radical is that of deoxyglucose, named the 1'-(2'-deoxy)gulopyranosidyl radical.

Useful aldoglycosidyl radicals can have one or more hydroxyl groups esterified by a lower alkanoyl radical such as formyl, acetyl, propionyl or hexanoyl, and also by a benzoyl radical. Aldoglycosidyl radicals are also useful when etherified by $C_1$–$C_6$ alkyl, especially methyl and ethyl radicals, whereas benzyl ethers are also useful. An acetal or ketal formed from a $C_1$–$C_6$ aldehyde or ketone such as formaldehyde or acetone is also contemplated. Ketals and acetals are formed from adjacent, cis-hydroxyl group such as those of ribose or glucose.

Suitable aldoglycosidyl radicals conform to the formula

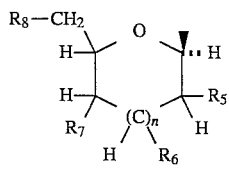

wherein n is one or zero;

$R_5$ is hydrogen, hydroxy, $C_1$–$C_6$ alkoxy such as methoxy and ethoxy (and others as described before), benzyloxy, $C_1$–$C_6$ alkanoyloxy such as formyloxy, acetoxy (and other $C_1$–$C_6$ alkyl carboxylate radicals as are described before) or benzoylxy.

$R_6$, when present, as well as $R_7$ and $R_8$ are preferably all the same. These radicals can be hydroxy, a $C_1$–$C_6$ alkyl ether ($C_1$–$C_6$ alkoxy) such as methoxy and ethoxy, a benzyl ether (benzyloxy), a $C_1$–$C_6$ alkanoyl radical ($C_1$–$C_6$ acyl) such as formyloxy, acetoxy, or a benzoate ester (benzoxy).

$R_5$ and $R_6$ (when present), or $R_5$ and $R_7$ (when $R_6$ is absent) can also together form a $C_1$–$C_6$ ketal or acetal from corresponding cis hydroxyl groups. Exemplary useful aldehydes and ketones include formaldehyde, acetaldehyde, acetone, 3-pentanone and cyclohexanone. The presence of a symmetrical acetal or ketal as is formed from formaldehyde, acetone, 3-pentanone or cyclohexanone is preferred.

When $R_5$ is other than hydrogen, it is preferred that $R_5=R_6$ (when present)=$R_7=R_8$. Except for acetals and ketals, an O-substituent, when present on one oxygen is preferably present on all available ring substituent oxygens.

The bonds of the above formula are not intended to convey any particular stereo specific configuration, except at the 1'-position at which the beta anomer is indicated.

In preferred practice, the aldoglycosidyl radical is selected from the group consisting of 1'-ribofuranosidyl, 1'-glucopyranosidyl, and 1'-(2'-deoxy)ribofuranosidyl radicals. Thus, preferably, when n is zero and $R_5$, $R_7$ and $R_8$ are all hydroxy, $R_6$ is absent, the aldoglycosidyl radical is selected from the group consisting of 1'-ribofuranosidyl; when n is zero, is hydrogen and $R_7$ and $R_8$ are hydroxy, $R_6$ is absent, the aldoglycosidyl radical is 2'-deoxy-1'-ribofuranosidyl; and when n is 1, and $R_5=R_6=R_7=R_8=$ hydroxy, 1'-glucopyranosidyl is the aldoglycosidyl radical.

As already noted, the aldoglycoside is bonded from its 1'-position to the 9-position of a guanine derivative and to the 8-position of isoxanthopterin. When named as a guanine derivative, that bonding can be described as a 9-1' bond, whereas when named as an isoxanthopterin derivative, that bonding can be described as an 8-1' bond. The beta anomer of the aldoglycoside is that preferred herein, although mixtures of alpha and beta anomers are also useful. The aldoglycoside utilized is in the D stereo configuration and that configuration is implied where it is not stated.

5. Exemplary Immune Response Enhancing Agents

Structural formulas of exemplary immune response-enhancing agents useful in a composition and method of this invention are shown below, wherein $R_1$, $R_2$ (where Z is $N_{-2}$), $R_3$ and $R_4$ are as shown in Table 1 following the structural formulas.

TABLE 1

| | R Group | $R_4$ |
|---|---|---|
| $R_2$ | methyl, X = O | 1'-ribofuranosidyl |
| $R_3$ | iso-propyl | 1'-lyxofuranosidyl |
| $R_2$ | n-butyl, X = O | 1'-arabinofuranosidyl |
| $R_3$ | n-hexyl | 1'-gulopyranosidyl |
| $R_1$ | nitro | 1'(2'-deoxy)ribofuranosidyl |
| $R_1$ | acetamido | 1'-xylofuranosidyl |
| $R_2$ | benzyl, X = O | 1'-allopyranosidyl |
| $R_3$ | phenethyl | 1'-mannopyranosidyl |
| $R_3$ | 2-phenylpropyl | 1'-(2',3',4',6'-tetra-O-acetyl)-glucopyranosidyl |
| $R_3$ | 2-phenyl-3-methylpentyl | 1'-(2',3',5'-tri-O-acetyl)-ribofuranosidyl |
| $R_3$ | o-xylyl | 1'-(2',3',5'-tri-O-acetyl)-arabinofuranosidyl |
| $R_3$ | p-(2-hexyl)phenyl | 1'-(2'-deoxy-3',5'-di-O-methyl)ribofuranosidyl |
| $R_3$ | N-methyl carboxamidomethyl | 1'-(2',3',4',6'-tetra-O-ethyl)glucopyranosidyl |
| $R_3$ | p-(trifluoromethyl)phenyl | 1'-(2',3',5'-tri-O-benzyl)-ribofuranosidyl |
| $R_3$ | o-methoxyphenyl | 1-(2',3',5'-tri-O-benzoyl)-ribofuranosidyl |
| $R_3$ | ethylenepropionate | 1'-(2',3',4',6'-tetra-O-ethyl) glucopyranosidyl |
| $R_3$ | p-(2-ethylbutoxy)-phenyl | 1'-(2'-deoxy-3',5'-di-O-methyl)ribofuranosidyl |
| $R_3$ | o-chlorophenyl | 1'-gulopyranosidyl |
| $R_3$ | m-bromophenyl | 1'-allopyranosidyl |
| $R_3$ | p-fluorophenyl | 1'-altropyranosidyl |
| $R_1$ | hydroxy | 1'-ribofuranosidyl |
| $R_1$ | mercapto | 1'-ribofuranosidyl |
| $R_1$ | methoxy | 1'-ribofuranosidyl |
| $R_1$ | iso-propoxy | 1'-xylofuranosidyl |
| $R_1$ | n-hexyloxy | 1'-(2'-deoxy)ribofuranosidyl |
| $R_1$ | benzoxy | 1'-ribofuranosidyl |
| $R_3$ | 2-phenylethoxy | 1'-lyxofuranosidyl |
| $R_3$ | 2-phenylpropoxy | 1'-(2'-deoxy)gulopyranosidyl |
| $R_1$ | chloro | 1'-ribofuranosidyl |
| $R_3$ | chloro | 1'-glucopyranosidyl |
| $R_1$ | bromo | 1'-(2'-deoxy)ribofuranosidyl |
| $R_3$ | fluoro | 1'-ribofuranosidyl |
| $R_1$ | iodo | 1'-ribofuranosidyl |
| $R_1$ | methylsulfido | 1'-ribofuranosidyl |
| $R_1$ | benzylsulfido | 1'-arabinofuranosidyl |
| $R_2$ | 2-chloroethyl, X = O | 1'-lyxofuranosidyl |
| $R_3$ | carbomethoxy | 1'-ribofuranosidyl |
| $R_3$ | carbethoxy | 1'-(2'-deoxy)ribofuranosidyl |

TABLE 1-continued

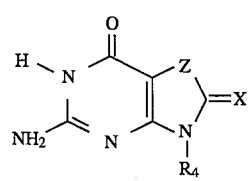

| R Group | R4 |
|---|---|
| R3  carbo-t-butoxy | 1'-xylofuranosidyl |
| R1  carbo-neo-pentoxy | 1'-glucopyranosidyl |
| R2  allyl, X = S | 1'-gulopyranosidyl |
| R3  n-butylcarboxy | 1'-mannopyranosidyl |
| R2  ethylenyl carbomethoxy, X = O | 1'-(2',3',4',6'-tetra-O-acetyl)glucopyranosidyl |
| R3  sec-butyleneyl carbohexyloxy | 1'-(2',3',5'-tri-O-acetyl)-ribofuranosidyl |
| R3  propyl | 1'-(2',3',5'-tri-O-acetyl)-arabinofuranosidyl |
| R3  hydroxymethyl | 1'-(2',3',5'-tri-O-methyl)-ribofuranosidyl |
| R2  allyl, X = O | 1'-(2',3',4',6'-tetra-O-benzyl) allopyranosidyl |
| R3  1,2-dihydroxyethyl | 1'-(2'-deoxy)ribofuranosidyl |
| R3  1,2,3-trihydroxypropyl | 1'-rhamnopyranosidyl |
| R2  2-hydroxyethyl, X = O | 1'-ribofuranosidyl |
| R2  ethylenyl carbethoxy, X = S | 1'-arabinofuranosidyl |
| R2  2-(N,N-dimethyl)-carboxamido, X = O | 1'-(2'-deoxy)gulopyranosidyl |
| R2  1-methyl-2-(N-morphylinyl) carboxamido, X = O | 1'-lyxofuranosidyl |
| R2  allyl, X = O | 1'-ribofuranosidyl |
| R2  allyl, X = S | 1'-ribofuranosidyl |
| R2  carbethoxymethyl, X = O | 1'-ribofuranosidyl |
| $R^1$  bromo | 1'-ribofuranosidyl |
| $R^1$  oxo, (hydroxyl) | 1'-ribofuranosidyl |
| $R^1$  methyl | 1'-ribofuranosidyl |
| $R^1$  methoxy | 1'-ribofuranosidyl |
| $R^1$  methylthio | 1'-ribofuranosidyl |
| $R^1$  thioxo (mercaptan) | 1'-ribofuranosidyl |
| $R^2$  methyl, X = O | 1'-ribofuranosidyl |
| $R^1$  bromo | 1'-(2',3',5'-tri-O-acetyl)-ribofuranosidyl |
| $R^1$  bromo | 1'-(2'-O-methyl)-ribofuranosidyl |
| $R^1$  bromo | 1'-(2'-deoxy)-ribofuranosidyl |
| R2  4-nitrobenzyl, X = O | 1'-ribofuranosidyl |
| R2  2-(4-chlorophenyl)-2-oxoethyl, X = O | 1'-ribofuranosidyl |
| R2  2,3-dihydroxypropyl, X = O | 1'-ribofuranosidyl |
| R2  2-chloroethyl, X = O | 1'-ribofuranosidyl |

Structural formulas of further examples of immune response-enhancing agents useful in a composition and method of this invention are shown below, wherein Z, X and $R_4$ are shown in Table 2 following the structural formula.

TABLE 2

| Z | X | R4 |
|---|---|---|
| O | O | 1'-ribofuranosidyl |
| O | O | 1'-lyxofuranosidyl |
| O | O | 1'-glucopyranosidyl |
| O | O | 1'-(2'-deoxy)ribofuranosidyl |
| S | O | 1'-gulopyranosidyl |
| S | O | 1'-allopyranosidyl |
| S | O | 1'-xylofuranosidyl |
| S | O | 1'-(2',3',4',6'-tetra-O-methyl)gulopyranosidyl |
| S | S | 1'-ribofuranosidyl |
| S | S | 1'-allopyranosidyl |
| S | S | 1'-(2',3',5'-tri-O-benzoyl)-galactopyranosidyl |
| O | S | 1'-mannopyranosidyl |
| O | S | 1'-ribofuranosidyl |
| O | S | 1'-(2',3',4',6'-tetra-O-benzyl)altropyranosidyl |

Particularly preferred 8-substituted guanine derivatives have $R_1$ groups selected from the group consisting of halo, hydroxy, mercapto, $C_1-C_6$ alkylthio, and $C_1-C_6$ alkoxy radicals at the 8-position.

For the tautomeric 7-substituted-8-oxo- and 8-thioxoguanine derivatives, the 8-substituent is preferably oxo, and the particularly preferred 7-substituents are $C_1-C_{10}$ alkyl, $C_3-C_{10}$ beta-alkenyl, halo $C_1-C_{10}$ alkyl, nitrobenzyl and benzyl radicals. Of those particularly preferred groups $C_3-C_6$ alkyl, $C_3-C_6$ beta-alkenyl, and halo $C_1-C_6$ alkyl are still more preferred. The 8-substituent of 7-oxa- and 7-thiaguanine derivatives is also preferably oxo, whereas a 7-oxaguanine derivative is preferred over a 7-thiaguanine derivative.

Particularly preferred isoxanthopterin 8-aldoglycosides are those having an $R_3$ group selected from the group consisting of hydrogen, hydroxy, $C_1-C_6$ alkyl, $C_1-C_6$ alkoxy carbonyl, and polyhydroxy $C_1-C_6$ alkyl bonded at the 6-position.

For each of the immune response-enhancing agents, the 9-1'-aldoglycoside or the 8-1'-aldoglycoside portions, as appropriate, of the molecule are preferably beta-1'-ribofuranosidyl, beta-1'-(2'-deoxy)ribofuranosidyl, or beta-1'-glucopyranosidyl. Exemplary of such particularly preferred materials are: 8-(1'-beta-D-ribofuranosidyl)isoxanthopterin; 8-(1'-beta-D-2'-deoxyribofuranosidyl)isoxanthopterin; 8-(1'-beta-D-glucopyranosidyl)isoxanthopterin; 6-hydroxy-8-(1'-beta-D-ribofuranosidyl)isoxanthopterin; 6-hydroxy-8-(1'-beta-D-2'-deoxyribofuranosidyl)-isoxanthopterin; 6-hydroxy-8-(1'-beta-D-glucopyranosidyl)isoxanthopterin; 6-methyl-8-(1'-beta-D-ribofuranosidyl)isoxanthopterin; 6-methyl-8-(1'-beta-D-glucopyranosidyl)isoxanthopterin; 6-methyl-8-(1'-beta-D-2-deoxyribofuranosidyl)isoxanthopterin; 6-carboxy-8 -(1'-beta-D-ribofuranosidyl)isoxanthopterin; 6-carboxy-8 -(1'-beta-D-glucopyranosidyl)isoxanthopterin; 6-carboxy-8-(1'-beta-D-2'-deoxyribofuranosidyl)-isoxanthopterin; 6-methoxycarbonyl-8-(1'-beta-D-ribofuranosidyl)isoxanthopterin; 6-methoxycarbonyl-8 -(1'-beta-D-2'-deoxyribofuranosidyl)isoxanthopterin; 6-methoxycarbonyl-8-(1'-beta-D-glucopyranosidyl)-isoxanthopterin; 6-hydroxycarbonyl-8-(1'-beta-D-2'-deoxyribofuranosidyl)isoxanthopterin; 6-hydroxy-8-(1'- beta-D-ribofuranosidyl)isoxanthopterin 6-hydroxycarbonyl-8-(1'-beta-D-glucopyranosidyl)isoxanthopterin; 6-methoxy-8-(1'-beta-D-2'-deoxyfuranosidyl)isoxanthopterin; 8-mercaptoguanosine [8-thioxoguanosine or 8-mercapto-9-(1'-beta-D-ribofuranosidyl)guanine]; 8-mercapto-9-(1'-beta-D-2'-deoxyribofuranosidyl)guanine; 8-mercapto-9-(1'-beta-D-glucopyranosidyl)guanine; 8-hydroxyguanosine [(8-oxoguanosine) or 8-hydroxy-9-(1'-beta-D-ribofuranosidyl)guanine]; 8-hydroxy-9-(1'-beta-D-2'-deoxyribofuranosidyl)guanine; 8-hydroxy-9-(1'-beta-D-glucopyranosidyl)guanine; 7-methyl-8-oxoguanosine [7-methyl-8-oxo-9-(1'-beta-D-ribofuranosidyl)guanine]; 7-methyl-8-oxo-9-(1'-beta-D-2'-deoxyribofuranosidyl) guanine; 7-methyl-8-oxo-9-(1'-beta-D-glucopyranosidyl)guanine; 7-allyl-8-oxoguanosine [7-allyl-8-oxo-9-(1'-beta-D-ribofuranosidyl)guanine]; 7-allyl-8-oxo-9-(1'-beta-D-2'-deoxyribofuranosidyl)-guanine; 7-allyl-8-oxo-9-(1'-beta-D-glucopyranosidyl)-guanine; 7-(4-nitrobenzyl)-8-oxoguanosine; 7-benzyl-8-oxoguanosine [7-benzyl-8-oxo-9-(1'-beta-D-ribofuranosidyl)guanine]; 7-benzyl-8-oxo-9-(1'-beta-D-2'-deoxyribofuranosidyl)guanine; 7-benzyl-8-oxo-9-(1'- beta-D-glucopyranosidyl)guanine; 8-bromoguanosine [8-bromo-9-(1'-beta-D-ribofuranosidyl)guanine]; 8-bromo-9 -(1'-beta-D-2'-deoxyribofuranosidyl)guanine; 8-bromo-9 -1'-beta-D-glucopyranosidyl)guanine; 8-chloroguanosine [8-chloro-9-(1'-beta-D-ribofuranosidyl)guanine]; 8-chloro-9-(1'-beta-D-2'-deoxyribofuranosidyl)guanine; 8-chloro-9-1'-beta-D-glucopyranosidyl)guanine; 8-methylthioguanosine [8-methylthio-9-(1'-beta-D-ribofuranqsidyl)guanine]; 8-methylthio-9-(1'-beta-D-2'-deoxyribofuranosidyl)guanine; 8-methylthio-9-(1'-beta-D-glucopyranosidyl)guanine; 7-(2-chloroethyl)-8-oxoguanosine; 7-oxa-8-oxoguanosine [7-oxa-8-oxo-9-(1' -beta-D-ribofuranosidyl)guanine]; 7-oxa-8-oxo-9-(1' -beta-D-2'-deoxyribofuranosidyl)guanine; and 7-oxa-8-oxo-9 -(1'-beta-D-glucopyranosidyl)guanine.

Most preferred immune response-enhancing agents useful herein are those compounds in which $R_4$ are the 1'-beta-D-ribofuranosidyl and 1'-beta-D-2'-deoxyribofuranosidyl radicals, in which $R_1$, $R_2$ and $R_3$ are particularly preferred, X is oxygen, and Z is N-$R_2$, as discussed before. These most preferred compounds have structures that conform to the formulas:

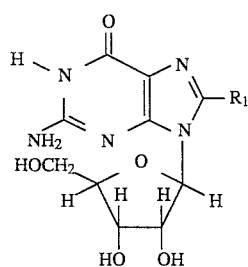

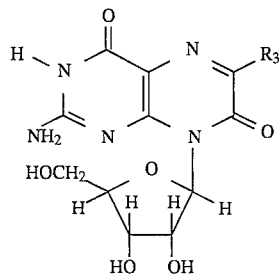

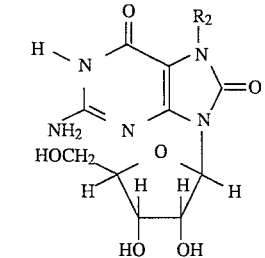

7-Allyl-8-oxoguanosine, 7-(2-chloroethyl)-8-oxoguanosine and 8-mercaptoguanosine are presently the most preferred immune response-enhancing agents.

Active ingredient drugs used in this invention comprise an in Vitro or in vivo effective (cytotoxic) amount of an anti-cancer drug and a CLL cell proliferation-inducing amount of an immune response-enhancing agent. Those ingredients preferably are admixed with a physiologically tolerably carrier for use in contacting the cancer cells. The two drugs are used separately and are separately compounded. A composition containing either drug can be administered perorally or parenterally to the host mammal in customary unit dosages; i.e., as a composition in unit dosage form comprising a physiologically tolerable carrier admixed with an effective amount of anti-cancer drug and a CLL cell proliferation-inducing amount of immune response-enhancing agent.

The term "unit dosage" and its grammatical equivalents as used herein refer to physically discrete units suitable as unitary dosages for human patients and other warm blooded animals, each unit containing a predetermined effective and potentiating amount of one or the other of the two active ingredients calculated to produce the desired therapeutic effect in association with the required physiologically tolerable carrier, e.g. a diluent or a vehicle. The specifications for the novel unit dosage forms of this invention are dictated by and are directly dependent on (a) the unique characteristics of the active ingredients and the particular therapeutic effect to be achieved, and (b) the limitations inherent in the art of compounding such an active ingredient for therapeutic use in humans and other animals. Examples of suitable unit dosage forms in accord with this invention are tablets, capsules, pills, powder packets, granules, wafers, and the like, segregated multiples of any of the foregoing, as well as liquid solutions, emulsions and suspensions.

The amount of each active ingredient that is administered in vivo depends on the age and weight of the patient, the particular B cell cancer to be treated and its severity, the frequency of administration, and the route of administration. More standardized amounts are used for in vitro contacting as are illustrated hereinafter and in the examples of the patents that disclose those immune response-enhancing agents.

Illustrative in vivo effective amounts of exemplary anti-cancer drugs are well known and some have already been provided.

The CLL cell proliferation-inducing (potentiating) dose range for a guanine derivative (formulas I and III) is about 0.01 to about 200 milligrams per kilogram of body weight (0.01–200 mg/kg), and that for an isoxanthopterin derivative (formula II) is about 0.01 to about 200 mg/kg. More preferably, a guanine derivative is administered at about 0.1 to about 25 mg/kg, whereas an isoxanthopterin is administered at about 0.1 to about 25 mg/kg. Most preferably, a guanine derivative is present at about 1 to about 15 mg/kg, whereas an isoxanthopterin is present at about 1 to about 10 mg/kg.

A human adult dose of an immune response-enhancing agent is in the range of about 5 to about 1,400 mg/day for a guanine derivative, and about 5 to about 1400 mg/day for an isoxanthopterin derivative, given either as a single dose or in 2 to about 8 divided doses that are given at about 12- to about 2-hour intervals. Veterinary dosages generally correspond to human dosages with the amounts administered being in proportion to the weight and metabolic rate of the animal as compared to adult humans. A substantially continuous or continual administration over an about 5- to about 14-day time period via intravenous infusion is also contemplated.

A composition can be a solid or a liquid. The two active ingredients can be individually admixed as a suspension of solids in a solid or liquid physiologically tolerable carrier, or dissolved as a solute or suspended in the carrier, or a combination thereof.

Physiologically tolerable carriers are well known in the art. Exemplary of liquid carriers are sterile aqueous solutions that can contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose and other solutes. These latter carriers are exemplified by Ringer's Injection, Dextrose Injection, Dextrose and sodium chloride Injection and Lactated Ringer's Injection.

Liquid compositions can also contain liquid phases in addition to and to the exclusion of water. Exemplary of such additional liquid phases are glycerin, vegetable oils such as sesame oil or cottonseed oil, and water-oil emulsions. Injectable oil-based compositions are particularly preferred for use with an immune response-enhancing agent as such compositions provide relatively long term and continual contacting of the cancer cells with that agent.

Exemplary solid carriers include those materials usually used in the manufacture of pills or tablets, and include corn starch, lactose, dicalcium phosphate, thickeners such as tragacanth and methylcellulose U.S.P., finely divided $SiO_2$, polyvinylpyrrolidone, magnesium stearate and the like. Additionally, the solid carrier can include biodegradable and nonbiodegradable polymers, polypeptide carriers, affinity carriers such as AFFI-GEL 601 (phenyl boronate resin available from Bio-Rad Laboratories, Richmond, Calif.), liposomes and synthetic polymers, as are known in the art. Antioxidants such as methylparaben and propylparaben can be present in both solid and liquid compositions, as can sweeteners such as cane or beet sugar, sodium saccharin, sodium cyclamate and the dipeptide methyl ester sweetener sold under the trademark NUTRASWEET (aspartame) by G. D. Searle Co.

An anti-cancer drug-containing composition useful herein is administered to a mammalian host perorally or parenterally, as noted before. A composition containing an immune response-enhancing agent useful in this invention can be administered once during a treatment regimen, such as a one month time period, more preferably a one to about two-week period of time is used for administration and contacting. More preferably still, an oil-based composition is used so that there is a continual release of the agent for continual contacting of the cancer cells. Multiple injections of an oil-based composition such as one injection per day over an about 5- to about 14-day period is particularly contemplated.

The immune response-enhancing agent administration is typically followed by a plurality of administrations of an in vivo effective amount of the anti-cancer drug alone, or admixed with a physiologically tolerable carrier. Typically, an immune response-enhancing agent of this invention is administered less frequently during a treatment period than is the anti-cancer drug without an immune response-enhancing agent, as dictated by the respective half-lives in vivo of the two active ingredients.

Best Mode For Carrying Out The Invention

Examples

The following examples relating to this invention are illustrative and should not, of course, be construed as specifically limiting the invention. Moreover, such variations of the invention, now known or later developed, that are within the purview of one skilled in the art are to be considered to fall within the scope of the present invention hereinafter claimed.

Example 1

Induction of Proliferative Activity by Immune Response-Enhancing Agents in Cells from Patients with Chronic Lymphocytic Leukemia Guanosine derivatives discussed in the before-mentioned U.S. patents were used in proliferation assays to measure the proliferative response of circulating chronic lymphocytic leukemia (CLL) cells isolated from CLL patients as described below. The assays were performed in the presence or absence of anti-cancer drugs added after the guanosine derivative to determine the effectiveness of the drugs on cultured CLL cells.

Circulating CLL cells were obtained from venous blood from consenting CLL patients. The cells were purified by Ficoll-diatrizoate density gradient centrifugation.

Two different culture media preparations were evaluated for supporting the maximal CLL proliferative response in the presence of the loxoribine 7-allyl- or 7-(2-chloroethyl)-8-oxoguanosine- For the two preparations, each 100 ml of medium contained 87.9 ml RPMI 1640 (Flow Laboratories, Rockville, Md.), 0.1 ml glutamine, 1.0 ml HEPES buffer (Microbiological Associates, Bethesda, Md.), 1.0 ml of water containing $10^4$ units of penicillin G and $10^4$ micrograms/ml (µg) of streptomycin, and 2-mercaptoethanol ($5\times10^5$M). For each solution, 10 ml of either fresh autologous heat-inactivated plasma (AP) or fetal calf serum (FCS) was then added to form a 10 percent solution. Isolated peripheral CLL cells were separately maintained at 37° C. in these three culture media formulations.

For the proliferation assays, 180 μl of peripheral CLL cells at a concentration of $1.1\times10^6$ cells/ml maintained in either AP or FCS were plated into microtiter wells of a 96 well plate. Loxoribine, for example, at 10× concentration was then added to individual microtiter wells to contact the cells for final concentrations of $1\times10^{-4}$M, $3\times10^{-4}$M and $1\times10^{-3}$M. The treated cultures were then maintained for two days in a humidified atmosphere of 5 percent $CO_2$ in air at 37° C., at which time 0.6 microcuries (μCi)/well of $^3$H-thymidine were added to each well. The cell cultures were maintained for one day to permit thymidine uptake into proliferating cells. The cells were then harvested with a PhD cell harvester (Cambridge Technology, Inc., Cambridge, Mass.) onto glass fiber filter disks. The disks were transferred to plastic scintillation vials, covered with liquid scintillation fluid and counted in a Beckman LS6800 liquid scintillation counter to determine the amount of $[^3H]$ thymidine uptake into the cells treated with loxoribine. The results of cells contacted with loxoribine were compared to control untreated cells.

The results of this preliminary assay showed that $[^3H]$ TdRuptake, an indicator for proliferation, of peripheral CLL cells from one CLL patient was enhanced in medium containing 10 percent autologous heat-inactivated plasma (AP) compared to that seen in the presence of 10 percent FCS. Although no proliferation relative to control values of about 200 and 400 cpm was seen in either AP or FCS cultures at a loxoribine concentration of $1\times10^{-4}$M, the maximum $[^3H]$-thymidine incorporation in AP-maintained cells, measured in counts per minute (cpm)/culture, peaked at a concentration of $3\times10^{-4}$M loxoribine with approximately 10,000 cpm/culture. The proliferation of cells in AP medium thereafter declined to approximately 8500 cpm/culture with $1\times10^{-3}$M loxoribine. The maximal proliferation of cells in 10 percent FCS was approximately 3000 cpm/culture at $1\times10^{-3}$M loxoribine. Thus, proliferation of peripheral CLL cells was maximized when the cells were maintained in AP medium and exposed to $3\times10^{-4}$M to $1\times10^{-3}$M loxoribine.

Different CLL patients exhibited slightly different dose response curves attributable to patient variation. For example, a separate CLL patient's cells maximally proliferated (28,000 cpm/culture) in AP medium with $1\times10^{-4}$M loxoribine compared to control values of 4,900 cpm. Although proliferation was still extensive in the presence of $3\times10^{-4}$M loxoribine (25,000 cpm/culture), only minimal proliferation occurred in the presence of $1\times10^{-3}$M loxoribine. No proliferation was seen in separate cultures maintained in FCS. Despite the patient variability with respect to the optimal dosage of loxoribine and the resultant thymidine incorporation, the culturing of cells in AP medium containing $3\times10^{-4}$ to $1\times10^{-3}$M loxoribine resulted in an induction of blast transformation and proliferation of peripheral CLL cells that normally proliferate extremely slowly. That the proliferative effect was due to loxoribine and not just the presence of autologous plasma was confirmed using negative controls containing AP without loxoribine.

In addition to measuring the proliferative effects induced by loxoribine, proliferation assays were performed as described above to determine the proliferative effects of the guanosing derivatives, 7-methyl-8-oxoguanosine and 7-(2-chloroethyl)-8-oxoguanosine. The compounds were assayed at a concentration of $3\times10^{-4}$M and compared to the results obtained with loxoribine at the same concentration.

Figure 6:
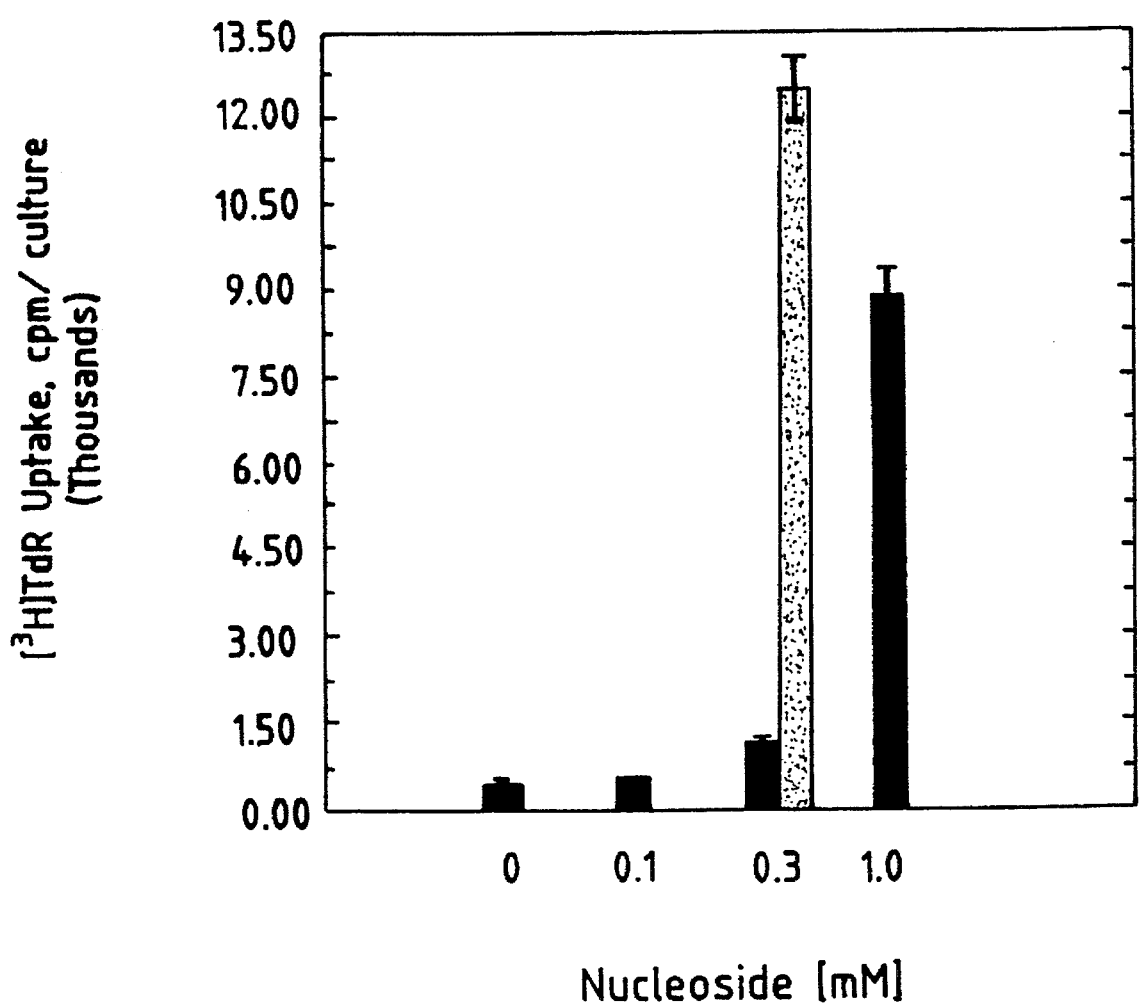
FIG. 6 is a graph similar to that shown in FIG. 5 except that circulating CLL cells from a patient whose cells undergo blast transformation and proliferation when contacted with loxoribine were contacted with varying concentrations of loxoribine (black bars) or 7-(2-chloroethyl)-8-oxoguanosine (dotted bar). The data are plotted as described in FIG. 5. The same negative control was used for both nucleosides.

Cells cultured in the absence of any added compound had 426±65 cpm/culture. At this dose, the derivative, 7-methyl-8-oxoguanosine (7m8oGuo), exhibited a slight, but not significant increase in proliferative activity (487±16 cpm/culture) compared to control. This result is not understood, as the mitogenicity of 7m8oGuo is only slightly less than that of loxoribine in the murine system. See Table 4 of U.S. Pat. No. 5,011,828. Only one concentration was assayed, and that concentration may have been suboptimal. Loxoribine-treated and the 7-(2-chloroethyl)-8-oxoguanosine-contacted cultures respectively had counts approximately 21-fold (8854 cpm/culture) and 29-fold (12,476±568 cpm/culture) as compared to control. Thus, other guanosine derivatives in addition to loxoribine stimulate proliferation of peripheral CLL cells isolated from CLL patients. The results using peripheral CLL cells from this patient are shown in FIG. 6 for loxoribine and 7-(2-chloroethyl)-8-oxoguanosine.

Figure 7:
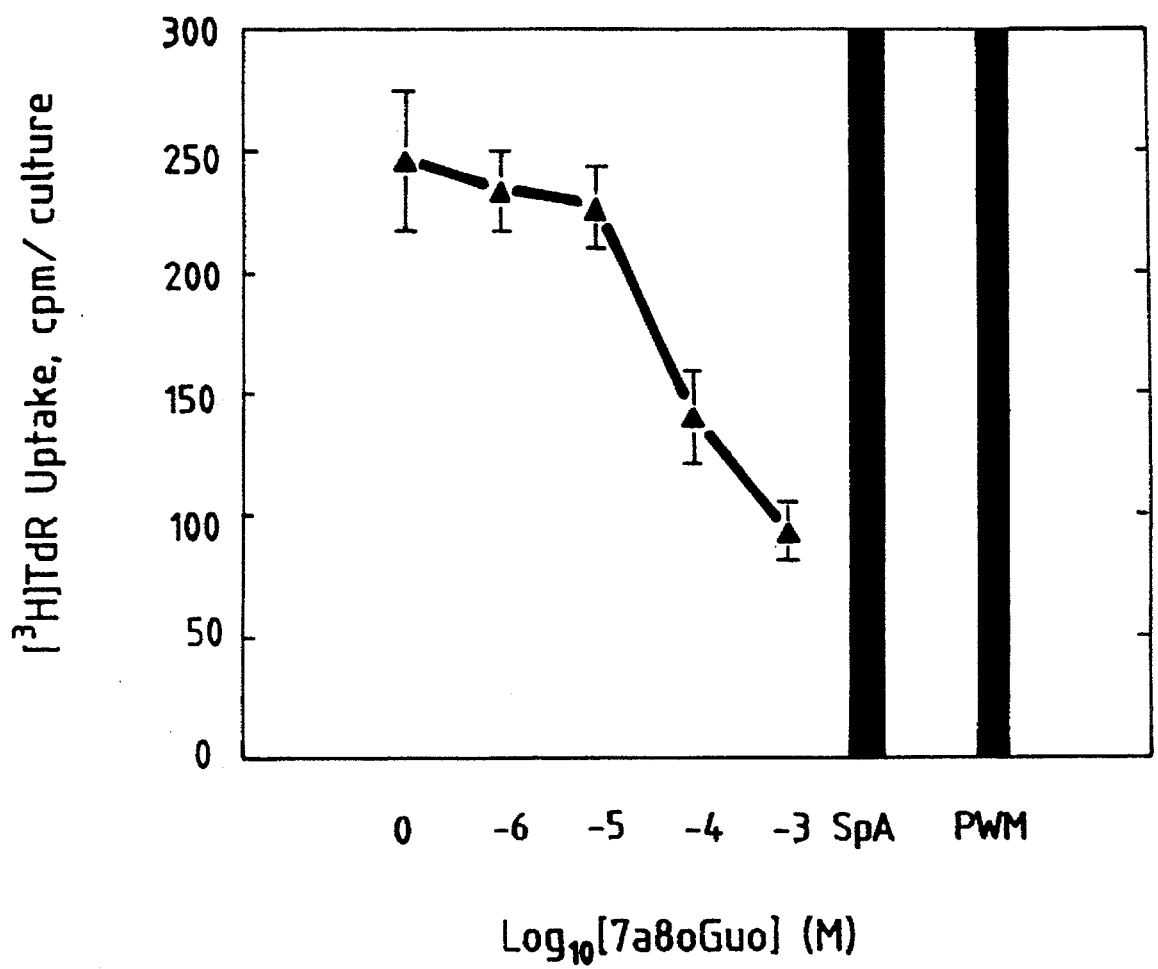
FIG. 7 is a graph showing the lack of proliferation as a decrease in tritiated thymidine uptake of peripheral blood lymphocytes (PBL) containing cancerous B cells from a patient having hairy cell leukemia contacted in vitro with loxoribine (7a8oGuo) in a culture medium containing 10 volume percent fetal calf serum. The uptake of radiolabelled thymidine [[$^3$H]TdR] is shown on the ordinate, versus the $\log_{10}$ of the molar (M) concentration of 7a8oGuo on the abscissa. The black bars above SpA (*S. aureas* protein A) and PWM (pokeweed mitogen) represent counts for similar cell cultures containing those non-pharmaceutically acceptable mitogens and not 7a8oGuo. The number of counts from cultures using SpA was 2,274±133, whereas the number of counts using PWM was 12,777±313.

A similar proliferation study was carried out using peripheral blood lymphocytes (PBL) of a patient having hairy cell leukemia that were contacted with various concentrations of loxoribine. The results of that study are shown in FIG. 7, wherein it is seen that increasing concentrations of loxoribine including those used to induce proliferation of peripheral CLL cells, e.g. $10^{-4}$–$10^{-3}$M, caused inhibition of proliferation and death of the hairy cells as was seen in FIG. 5 where 8-mercaptoguanosine was used to kill cancerous murine B cells.

Example 2

Enhancement of Cytotoxic Effects of Various Cytotoxic Agents by Loxoribine-Treated Cells from Patients with Chronic Lymphocytic Leukemia Treatment of CLL patients with anti-cancer drugs is non-curative and of limited effectiveness. Circulating CLL cells proliferate slowly and therefore are not responsive to cytotoxic drugs that act at specific stages of the cell cycle and act preferentially on rapidly proliferating cells. To improve the efficacy of treatment of patients with CLL, peripheral CLL cells were collected and were first exposed to proliferation-inducing amounts of an immune response-enhancing agent such as loxoribine followed by exposure to various anti-cancer drugs. The advantage provided by this approach is the possibility of curative therapy for CLL or at least a major diminution in tumor burden, an improvement in the quality of life and the prolongation of the patient's survival time after diagnosis. The methods for screening for effective cytotoxic agents used in conjunction with proliferation-inducing compounds are described herein.

A two stage culture assay was used to measure the sensitivity of loxoribine-responsive peripheral CLL cells from CLL patients to anti-cancer drugs. In culture tubes, 1 ml cultures containing 900 μl of isolated circulating CLL cells at $1.1\times10^6$ cells/ml and 100 μl of 10× loxoribine were prepared as described in Example 1 and were maintained in culture for two days. At that time, one hundred μl of cytotoxic agents diluted in AP culture medium were separately added to loxoribine-stimulated and control CLL cell cultures. After maintaining the cells for selected periods of time in the presence of selected anti-cancer drugs, the cells were stained with propidium iodide (2 μg/ml) and analyzed for viability by fluorescence activated cell sorting (FACS). In the other assays, 8 μl of 0.4 percent trypan blue dye were added to the culture instead of the propidium iodide. The stained and unstained cells were counted under a microscope.

For each anti-cancer drug evaluated, the assays were performed in the absence of loxoribine, in $3\times10^{-4}$M (0.3 mM) loxoribine or in $1\times10^{-3}$M (1 mM) loxoribine. The results were compared to similarly treated control cultures without cytotoxic agents. The percentage of viable CLL cells after 1, 3, 4 or 5 days of contact with anti-cancer drugs was determined by FACS as described above. The results of these studies using cells from different patients are shown in FIGS. 1, 2 and 3.

In FIG. 1, the results of two-stage viability assays are shown for a CLL patient's peripheral CLL cells that do not proliferate or undergo blast transformation when contacted with a proliferation-inducing amount of loxoribine. The CLL cells were maintained for 2 days in loxoribine at either zero, 0.3 mM or 1.0 mM in concentration followed by one additional day in the presence of the following anti-cancer drugs for a total of 3 days from initiation of the culture (the anti-cancer drug names and final concentrations of which are shown in parentheses): VP-16 (etoposide; 10 µg/ml); CTX (cytoxan; $10^{-6}$M); DXR (adriamycin; $10^{-5}$M); VCR (vincristine; $10^{-6}$M); CIS-P (cisplatin; $10^{-6}$M); CHL (chlorambucil; $10^{-5}$); and MTX (methotrexate; $10^{-6}$M). The data are plotted in a bar graph where percent viable cells are plotted on the Y-axis (ordinate) against the assayed anti-cancer drug with loxoribine (0.3 mM in the cross-hatched bars or 1.0 mM in the diagonally lined bars) or without loxoribine (blackened bars). The data are compared to CLL cells either contacted with loxoribine or in medium alone (indicated as "none" on the graph).

Evident from the graph of FIG. 1 is that loxoribine-contacting alone at either concentration causes a significant decrease in peripheral CLL cell viability from approximately 55 percent down to approximately 40 percent. Thus, loxoribine causes CLL cell death after three days in culture.

The cytotoxic effects of loxoribine-treated cells were enhanced, however, if maintained in the presence of added anti-cancer drugs. In particular, the drugs, DXR, VCR, CIS-P, and CHL in the presence of either 0.3 mM or 1.0 mM loxoribine resulted in enhanced cellular cytotoxicity as measured by a decrease in cell viability. MTX was effective in the presence of 1.0 mM loxoribine.

In addition, the effect of the cytotoxicity as measured by a decrease in viability was enhanced by the cytotoxic agents themselves as compared to untreated cells. The most potent cytotoxic agent in this respect was DXR where only 20 percent of peripheral CLL cells were viable. The cytotoxic effect was further enhanced by pre exposure to loxoribine resulting in less than 10 percent viable cells. In contrast, VCR and CHL were not effective when used to treat CLL cells alone, but in conjunction with loxoribine contacting, the viability of the cells contacted with both drugs decreased. Thus, treatment of peripheral CLL cells with loxoribine followed by contact of those cells with anti-cancer drugs resulted in an augmentation of drug-induced cytotoxicity.

When a different CLL patient's peripheral CLL cells that were shown to undergo blast transformation and proliferation when contacted with loxoribine were contacted with anti-cancer drugs for 4 days following loxoribine contact for a total incubation period of 6 days, the cytotoxic effects of selected anti-cancer drugs were again enhanced by the pretreatment of cells with loxoribine. The data are shown in FIG. 3 plotted as described for FIG. 1. The cytotoxic agents tested included DEX (dexamethasone; $2\times10^{-7}$M and $2\times10^{-6}$M), VP-16 (etoposide; 2 µg/ml), CTX (cytoxan; $2\times10^{-7}$M and $\times10^{-6}$M), DXR (doxorubicin; $2\times10^{-7}$M) and VCR (vincristine; $1\times10^{-6}$M). The drugs, Dex and VCR resulted in significant cell killing in the absence of loxoribine. DXR was less effective. The effects of enhanced cytotoxicity by contact of anti-cancer drugs with loxoribine-contacted cultures were dramatic as compared to the results shown in FIG. 1. The variability of percentage of cell death and the independent effects of the anti-cancer drugs are attributable to patient variability.

The cytotoxic effects of VP-16 alone or in conjunction with loxoribine-contacting of a CLL patient's peripheral CLL cells were evaluated over a total time course of 23 days after culture initiation. These peripheral CLL cells responded to loxoribine contacting by undergoing blast transformation and proliferation. The two-stage assay was performed as described above where VP-16 was added to cultures of cells that were either untreated or loxoribine-treated for two days. Control cultures included cells cultured in medium throughout the selected time course or exposed to loxoribine for the entire time course. At selected days after the initiation of the cultures, cells were harvested, stained and analyzed by trypan blue dye exclusion as described above.

Figure 4:
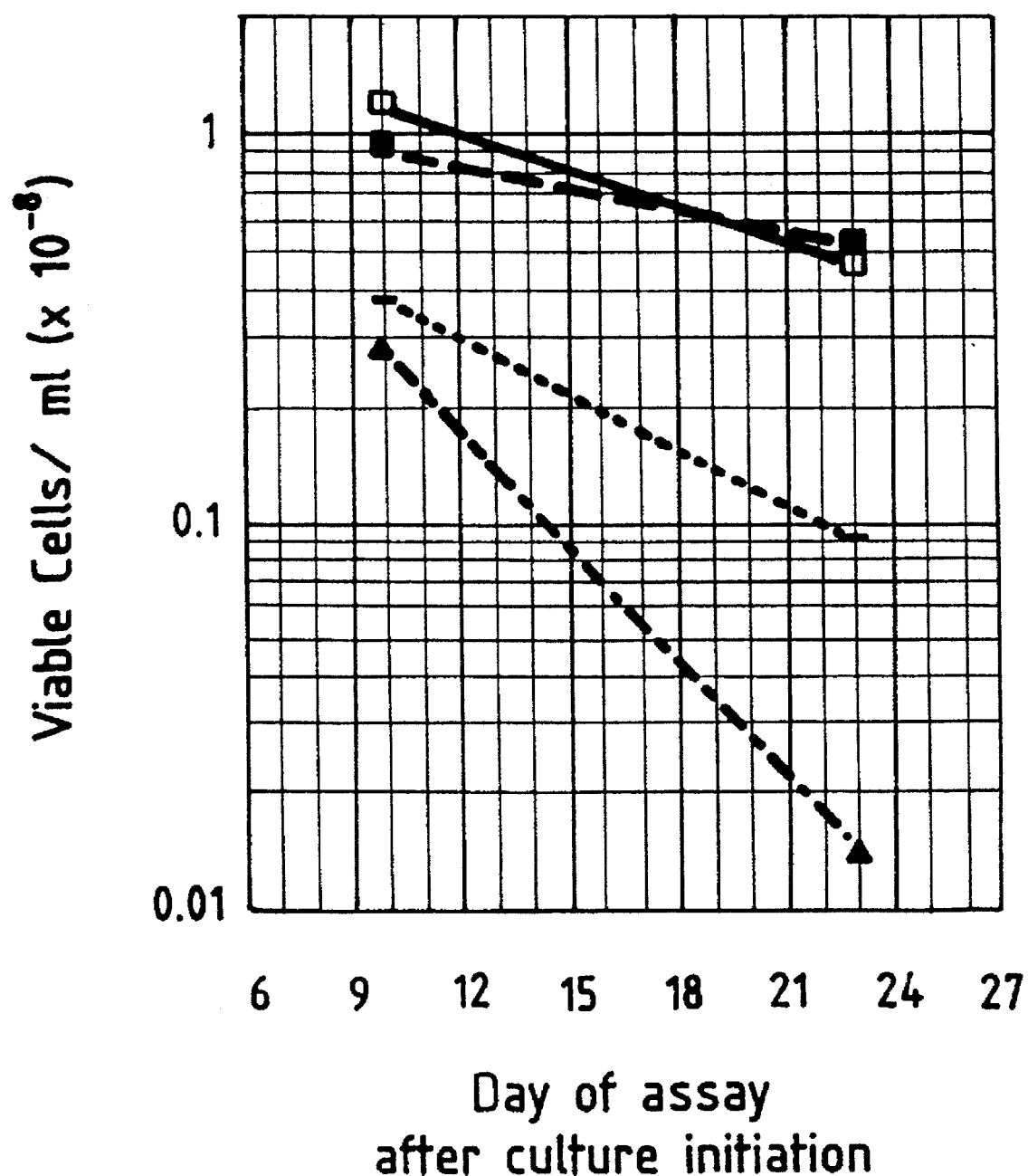
FIG. 4 illustrates the results of a two-stage assay performed as described in FIG. 1 and Example 2 where anti-cancer drug VP-16 was contacted with cultures of peripheral CLL cells that undergo blast transformation and proliferation when contacted with loxoribine were either untreated or loxoribine-contacted. Control cultures included cells cultured in medium throughout the selected time course (darkened squares) or contacted only with loxoribine ($3\times10^{-4}$M) for the first two days of time course (open squares). CLL cells cultured in medium plus VP-16 (10 μg/ml) are shown as crosses, whereas CLL cells cultured in medium plus VP-16 (10 μg/ml) plus loxoribine ($3\times10^{-4}$M) are shown as darkened triangles. Cells were harvested, stained and analyzed by trypan blue dye exclusion as described in Example 2 on days 7 and 23 after initiation of the culture. The viable cells/ml$\times10^{-6}$ are plotted on the Y-axis against day of assay after culture initiation plotted on the X-axis.

The results of the extended time course of 23 days are shown in FIG. 4. The viable cells/ml$\times10^{-6}$ are plotted on the Y-axis against day of assay after culture initiation plotted on the X-axis. Loxoribine treatment alone was somewhat cytotoxic to the cells throughout the time course as evidenced by the equivalent decrease of cell viability to cells cultured in medium alone.

Contacting of cells with VP-16 alone resulted in a decreased cell viability from the day 7 compared to control cultures. The cell viability slightly decreased linearly up to 23 days in culture. VP-16 contact with loxoribine-contacted cells, however, resulted in a synergistic response where the number of viable cells were about 30 percent that of control cells at day 10 but were approximately 25-fold less at day 14 (not shown), and 40-fold less at day 23. This synergism that increased over time was even more prominent in a separate assay of another patient's cells.

Despite some variability evidenced between individual CLL patients, an enhanced cytotoxic effect was detected with treatment of loxoribine-contacted peripheral CLL cells with a particular anti-cancer drug.

Further studies similar to those already discussed were carried out using cells from the four patients of FIGS. 1–4 plus two further CLL patients, and culture conditions as discussed generally before. Thus, cells were cultured at $10^6$/ml. Each group of cells was divided into four culture types. One served as control, another had loxoribine added as the immune response-enhancing agent, the third received an anti-cancer drug, and the fourth received both loxoribine and the anti-cancer drug. Volumes in each culture were equalized by addition of required amounts of medium. All of the cultures for a particular patient's cells were begun on the same day, and were assayed on the same day. Cells treated with both loxoribine and the anti-cancer drug were contacted first for two days with loxoribine and the anti-cancer drug was added at the beginning of the third day. Cells from patients VMi, JW and JF were contacted with 1 mM loxoribine, whereas cells from patients KS, VMu and WH were contacted with 0.3 mM loxoribine. Here, CLL cells were considered to proliferate when radio-labeled thymidine uptake in the presence of loxoribine contact was at least 3.5 times that in the absence of loxoribine.

The data of the table below illustrate the percentage of non-viable cells in control (no additive) cultures compared to cultures containing loxoribine as the immune response-enhancing agent alone, one or more separate anti-cancer drugs alone, or culture and contacting first with loxoribine, followed by contacting of those cells the same anti-cancer drug for 1–4 days. Data were taken 3–7 days after the initiation of culture with the number of total days of culture being shown in parentheses in the last column. Abbreviations for anti-cancer drugs are as before-discussed, with concentrations for each study in parentheses.

expressed on substantially all of the cells at all concentrations of loxoribine, including zero. Only about 46 percent of the cells exhibited CD38 in the absence of loxoribine, with substantially all of the cells expressing that antigen in the presence of loxoribine at each concentration.

The cells also exhibited a dose-dependent enhancement of those expressed antigens. For CD22 and CD23, the enhancement was about 3.5-fold over control; for CD25, the enhancement was about 17-fold over control; for CD38, the enhancement was about 23-fold over control; and for CD54, the enhancement was about 6-fold over control. For CD23,

TABLE

Percent Non-Viable Cells in Culture

| CLL Patient | Control | Loxoribine | Anti-Cancer Drug | Loxoribine + Anti-Cancer Drug[1] | CLL Prolif.[2] | Measurement Method[3] |
|---|---|---|---|---|---|---|
| VMi | 52.6 | 77.1 | DXR: 73.9 | +DXR (0.2 μM): 86.9 | Yes | PI (6) |
|  |  |  | Dex: 78.6 | +Dex (2 μM): 85.4 |  |  |
| JW | 15.6 | 20.7 | CDDP: 16.7 | +CDDP (10 μM): 44.3 |  |  |
|  |  |  | MTX: 22.8 | +MTX (10 μM): 45.2 | No | Pi (5) |
|  |  |  | AraC: 84.1 | +AraC (10 μM): 86.6 |  |  |
| JF | 44.0 | 56.8 | DXR: 80.9 | +DXR (10 μM): 93.0 |  |  |
|  |  |  | CHL: 47.6 | +CHL (10 μM): 80.6 | No | PI (3) |
|  |  |  | VCR: 50.0 | +VCR (1 μM): 72.8 |  |  |
| KS | 70.8 | 79.3 | DXR: 99.0 | +DXR (10 μM): 99.7 |  |  |
|  |  |  | CTX: 64.4 | +CTX (1 μM): 79.4 | Yes | PI (3) |
|  |  |  | CDDP: 80.1 | +CDDP (1 μM): 84.8 |  |  |
| VMu | 14.0 | 60.0 | DXR: 34.0 | +DXR (1 μM): 50.0 |  |  |
|  |  |  | MTX: 6.9 | +MTX (1 μM): 25.8 | No | TB (6) |
|  |  |  | 2-CdA: 16.4 | +2-CdA (10 μM): 27.3 |  |  |
| WH | 27.2 | 43.4 | VP-16: 69 | +VP-16 (10 μM): 96.3 | Yes | TB (7) |

[1]The designation "+" with a drug abbreviation indicates a prior loxoribine contacting followed by contacting with the indicated anti-cancer drug at the parenthesized concentration.
[2]CLL proliferation (Prolif.) indicated by at least a 3.5-fold uptake of radio-labeled thymidine when separately contacted with loxoribine as compared to uptake without loxoribine.
[3]PI = propidium iodide staining assayed by FACS; TB = trypan blue exclusion assay carried out on a microscope slide; parenthesized day of assay after culture initiation.

AS is seen from the above data, greater cell death was always found for the combined regimen as compared to the use of the anti-cancer agent alone. In five of the six studies, the combined therapy also resulted in greater cell death than did loxoribine alone. The data also show a trend toward greater overall cell death from those cells that proliferated when contacted with the immune response-enhancing agent.

Example 3

Up-Regulation of Surface Antigens on Human CLL Cells by Contacting with an Immune Response-Enhancing Agent Human CLL cells ($10^6$/ml) that proliferated in the presence of an immune response-enhancing agent were cultured in the presence of varying amounts of loxoribine as an immune response-enhancing agent at four concentrations: zero, $1\times10^{-4}$, $3\times10^{-3}$ and $1\times10^{-3}$M as discussed previously. The cells were then assayed by FACS analysis using antigen-specific antibodies linked to fluorescent indicators. The assays were graciously performed by Dr. Susan Wormsley of Cytometry Associates, San Diego, Calif.

This FACS study provided two types of information as to the expression of cell surface antigens; i.e., the percentage of cells that exhibited the antigen, and a relative intensity of fluorescence exhibited, which correlates to the relative number of antigen molecules expressed on the cell surface. The study showed that CD22, CD23, CD25 and CD54 were CD38 and CD54, the enhancement peaked at 0.1–0.3 mM and then dropped at the highest concentration, whereas no drop was noted for CD22, and CD25 appeared to plateau in the concentration range studied.

Lambda light chain, HLA-DR, CD5, CD11c and CD20 surface antigens typically exhibited one or more of the following results after contacting with loxoribine; fewer cells with the antigen, less enhancements, or enhancements that were not dose-dependent.

The present invention has been described with respect to preferred embodiments. It will be clear to those skilled in the art that modifications and/or variations of the disclosed subject matter can be made without departing from the scope of the invention set forth herein.

What is claimed is:

1. A process for killing cancerous B cells that comprises:

(a) contacting in an aqueous medium a CLL cell proliferation-inducing amount of an immune response-enhancing agent with cancerous B cells of a host mammal that do not undergo blast transformation and proliferation when contacted with an immune response-enhancing agent; and (b) maintaining said contact under biological culture conditions for a time period sufficient for the contacted cancerous B cells to die;

said immune response-enhancing agent having a structure that corresponds to a formula

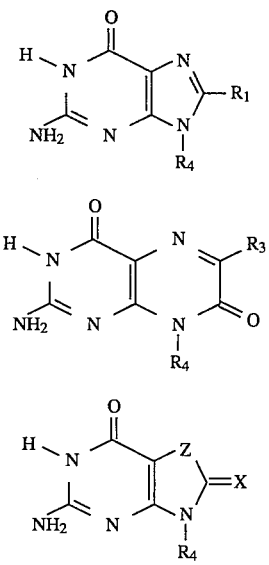

wherein

Z is O, S or N—$R_2$;

$R_1$ contains up to about 20 atoms and has a Hammett substituent sigma constant for ionization of a meta-substituted benzoic acid that is greater than that of hydrogen;

$R_2$ is a radical having a length up to about that of an n-decyl group that is selected from the group consisting of $C_1$–$C_{10}$ alkyl, $C_3$–$C_{10}$ beta-alkenyl, phenyl-substituted $C_3$–$C_6$ beta-alkenyl, benzyl, $C_1$–$C_6$ alkoxybenzyl, nitrobenzyl, hydroxy $C_1$–$C_{10}$ alkyl, polyhydroxy $C_1$–$C_{10}$ alkyl, halo $C_1$–$C_{10}$ alkyl, polyhalo $C_1$–$C_{10}$ alkyl, $C_1$–$C_6$ alkylene $C_1$–$C_6$ alkylcarboxylate, $C_1$–$C_{10}$ alkanoyl, $C_1$–$C_6$ alkoxy $C_1$–$C_6$ alkylenecarbonyl, and $C_1$–$C_6$ alkylenecarboxamido in which the carboxamido group has the formula $CONR_9R_{10}$ wherein $R_9$ and $R_{10}$ are the same or different and are selected from the group consisting of hydrogen and $C_1$–$C_6$ alkyl or $NR_9R_{10}$ together form a heterocyclic ring having five or six atoms in the ring;

X is oxygen or sulfur;

$R_3$ is a radical selected from the group consisting of hydrogen, $C_1$–$C_6$ alkyl, hydroxy $C_1$–$C_6$ alkyl, polyhydroxy $C_1$–$C_6$ alkyl, phenyl, phenyl-$C_1$–$C_6$ alkylene, $C_1$–$C_6$ alkylphenyl, $C_1$–$C_6$ alkoxyphenyl, halophenyl, trifluoromethylphenyl, hydroxy, oxo (O=), $C_1$–$C_6$ alkoxy, phenyl-$C_1$–$C_6$ alkoxy, halo, mercapto, thioxo (S=), $C_1$–$C_6$ alkylthio, phenyl-$C_1$–$C_6$ alkylthio, $C_1$–$C_6$ alkanoyl ($C_1$–$C_6$ acyl), $C_1$–$C_6$ alkoxy carbonyl, $C_1$–$C_6$ alkylene $C_1$–$C_6$ alkylcarboxylate, $C_1$–$C_6$ alkoxy $C_1$–$C_6$ alkyl carbonyl, and $C_1$–$C_6$ alkyl carboxamido in which the carboxamido group has the formula $CONR_9R_{10}$ wherein $R_9$ and $R_{10}$ are the same or different and are selected from the group consisting of hydrogen and $C_1$–$C_6$ alkyl, or $NR_9R_{10}$ together form a heterocyclic ring having five or six atoms in the ring;

$R_4$ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl, and their O-substituted $C_1$–$C_6$ alkyl, $C_1$–$C_6$ alkanoyl, benzyl, benzoyl and $C_1$–$C_6$ acetal or ketal derivatives, an O-substituent other than an acetal or ketal, if present on one oxygen, being present on all available ring substituent oxygens;

the pharmaceutically acceptable salts of said agent; and the tautomers thereof, said immune response-enhancing agent being free from ionic charge in water at pH 7.2–7.4.

2. The process according to claim 1 wherein said immune response-enhancing agent has a structure that corresponds to a formula

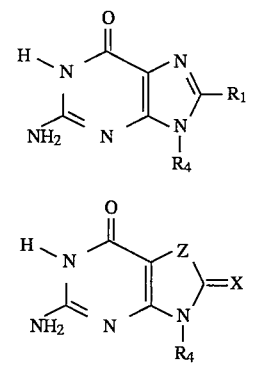

wherein Z is N—$R_2$ and =X is =O.

3. The process according to claim 2 wherein $R_4$ is 1'-aldopentosidyl in mono-deoxygenated 1'-aldopentosidyl.

4. The process according to claim 3 wherein $R_1$ is OH or SH.

5. The process according to claim 3 wherein $R_2$ is selected from the group consisting of $C_1$–$C_{10}$ alkyl, $C_3$–$C_{10}$ beta-alkenyl and halo $C_1$–$C_{10}$ alkyl.

6. The process according to claim 1 wherein said immune response-enhancing agent is 7-allyl-8-oxoguanosine, 7-(1-chloroethyl)-8-oxoguanosine or 8-mercaptoguanosine.

7. The process according to claim 1 wherein said contacting is carried out in vitro in a mammalian cell culture medium.

8. The process according to claim 7 wherein said mammalian cell culture medium includes about 5 to about 15 volume percent fetal calf serum or autologous plasma.

9. The process according to claim 1 wherein said cancerous B cells are circulating chronic lymphocytic leukemia, hairy cell leukemia cells or non-Hodgkins' leukemia cells.

10. The process according to claim 1 including the further steps of contacting the maintained cells of step (b) with a cytotoxic amount of an anti-cancer drug or a two portion conjugate molecule, one portion binding to a cell surface antigen that is expressed in enhanced amounts due to said contacting of step (a) and the other portion being an anti-cancer drug or a cytoxic agent, said further contacting being at a time about 1 to about 4 days after the first contacting of step (a), and maintaining the anti-cancer drug-contacted cells under biological culture conditions for a time period sufficient for those cells to die.

11. The process according to claim 10 wherein said immune response-enhancing agent has a structure that corresponds to a formula

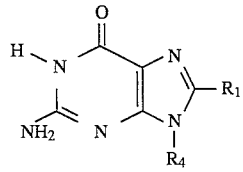

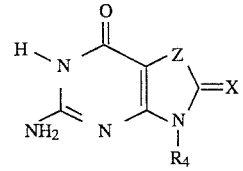

wherein Z is N—$R_2$ and =X is =O.

12. The process according to claim 11 wherein $R_4$ is 1'-aldopentosidyl in mono-deoxygenated 1'-aldopentosidyl.

13. The process according to claim 12 wherein $R_1$ is OH or SH.

14. The process according to claim 12 wherein $R_2$ is selected from the group consisting of $C_1$–$C_{10}$ alkyl, $C_3$–$C_{10}$ beta-alkenyl and halo $C_1$–$C_{10}$ alkyl.

15. The process according to claim 10 wherein said immune response-enhancing agent is 7-allyl-8-oxoguanosine, 7-(1-chloroethyl)-8-oxoguanosine or 8-mercaptoguanosine.

16. The process according to claim 10 wherein said cancerous B cells are circulating chronic lymphocytic leukemia, hairy cell leukemia cells or non-Hodgkins' leukemia cells.

17. The process according to claim 10 wherein said anti-cancer drug is selected from the group consisting of etoposide, cytoxan, adriamycin, vincristine, cisplatin, chlorambucil, methotrexate, carmustine, cytarabine, dexamethasone and doxorubicin.

18. A process for killing chronic lymphocytic leukemia (CLL) cells that comprises:

(a) contacting in an aqueous medium a proliferation-inducing amount of an immune response-enhancing agent with human CLL cells that undergo blast transformation and proliferation when contacted with said immune response-enhancing agent with a proliferation-inducing amount of an immune response-enhancing agent;

(b) maintaining said contact under biological culture conditions for a time period sufficient for said contacted CLL cells to proliferate and form blasts;

(c) contacting said blasts with a cytotoxic amount of an anti-cancer drug; and (d) maintaining said contact with said anti-cancer drug under biological culture conditions for a time period for said contacted blast cells to die, said immune response-enhancing agent having a structure that corresponds to a formula

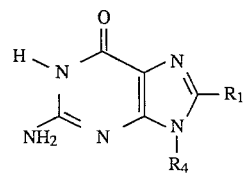

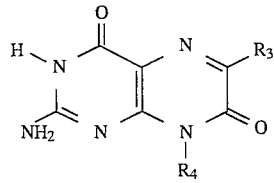

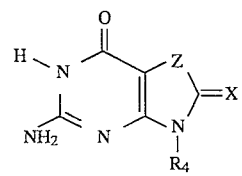

wherein

Z is O, S or N—$R_2$;

$R_1$ contains up to about 20 atoms and has a Hammett substituent sigma constant for ionization of a meta-substituted benzoic acid that is greater than that of hydrogen;

$R_2$ is a radical having a length up to about that of an n-decyl group that is selected from the group consisting of $C_1$–$C_{10}$ alkyl, $C_3$–$C_{10}$ beta-alkenyl, phenyl-substituted $C_3$–$C_6$ beta-alkenyl, benzyl, $C_1$–$C_6$ alkoxybenzyl, nitrobenzyl, hydroxy $C_1$–$C_{10}$ alkyl, polyhydroxy $C_1$–$C_{10}$ alkyl, halo $C_1$–$C_{10}$ alkyl, polyhalo $C_1$–$C_{10}$ alkyl, $C_1$–$C_6$ alkylene $C_1$–$C_6$ alkylcarboxylate, $C_1$–$C_{10}$ alkanoyl, $C_1$–$C_6$ alkoxy $C_1$–$C_6$ alkylenecarbonyl, and $C_1$–$C_6$ alkylenecarboxamido in which the carboxamido group has the formula $CONR_9R_{10}$ wherein $R_9$ and $R_{10}$ are the same or different and are selected from the group consisting of hydrogen and $C_1$–$C_6$ alkyl, or $NR_9R_{10}$ together form a heterocyclic ring having five or six atoms in the ring;

X is oxygen or sulfur;

$R_3$ is a radical selected from the group consisting of hydrogen, $C_1$–$C_6$ alkyl, hydroxy $C_1$–$C_6$ alkyl, polyhydroxy $C_1$–$C_6$ alkyl, phenyl, phenyl-$C_1$–$C_6$ alkylene, $C_1C_6$ alkylphenyl, $C_1$–$C_6$ alkoxyphenyl, halophenyl, trifluoromethylphenyl, hydroxy, oxo (O=), $C_1$–$C_6$ alkoxy, phenyl-$C_1$–$C_6$ alkoxy, halo, mercapto, thioxo (S=), $C_1$–$C_6$ alkylthio, phenyl-$C_1$–$C_6$ alkylthio, $C_1$–$C_6$ alkanoyl ($C_1$–$C_6$ acyl), $C_1$–$C_6$ alkoxy carbonyl, $C_1$–$C_6$ alkylene $C_1$–$C_6$ alkylcarboxylate, $C_1$–$C_6$ alkoxy $C_1$–$C_6$ alkyl carbonyl, and $C_1$–$C_6$ alkyl carboxamido in which the carboxamido group has the formula $CONR_9R_{10}$ wherein $R_9$ and $R_{10}$ are the same or different and are selected from the group consisting of hydrogen and $C_1$–$C_6$ alkyl or $NR_9R_{10}$ together form a heterocyclic ring having five or six atoms in the ring;

$R_4$ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl, and their O-substituted $C_1$–$C_6$ alkyl, $C_1$–$C_6$ alkanoyl, benzyl, benzoyl and $C_1$–$C_6$ acetal or ketal derivatives, an O-substituent other than an acetal or ketal, if present on one oxygen, being present on all available ring substituent oxygens;

the pharmaceutically acceptable salts of said agent; and the tautomers thereof, said immune response-enhancing agent being free from ionic charge in water at pH 7.2–7.4.

19. The process according to claim 18 wherein said immune response-enhancing agent has a structure that corresponds to a formula

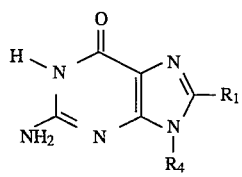

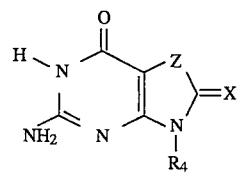

wherein Z is N-$R_2$ and =X is =O.

20. The process according to claim 19 wherein $R_4$ is 1'-aldopentosidyl in mono-deoxygenated 1'-aldopentosidyl.

21. The process according to claim 20 wherein $R_1$ is OH or SH.

22. The process according to claim 20 wherein $R_2$ is selected from the group consisting of $C_1$–$C_{10}$ alkyl, $C_3$–$C_{10}$ beta-alkenyl and halo $C_1$–$C_{10}$ alkyl.

23. The process according to claim 18 wherein said immune response-enhancing agent is 7-allyl-8-oxoguanosine, 7-(1-chloroethyl)-8-oxoguanosine or 8-mercaptoguanosine.

24. The process according to claim 18 wherein said contacting is carried out in vitro in a mammalian cell culture medium.

25. The process according to claim 24 wherein said mammalian cell culture medium includes about 5 to about 15 volume percent fetal calf serum or autologous plasma.

26. The process according to claim 18 including the further steps of contacting the maintained cells of step (b) with a cytotoxic amount of an anti-cancer drug or a two portion conjugate molecule, one portion binding to a cell surface antigen that is expressed in enhanced amounts due to said contacting of step (a) and the other portion being an anti-cancer drug or a cytoxic agent, said further contacting being at a time about 1 to about 4 days after the first contacting of step (a), and maintaining the anti-cancer drug-contacted cells under biological culture conditions for a time period sufficient for those cells to die.

27. A process for killing cancerous B cells that comprises:
(a) contacting in an aqueous medium a CLL cell proliferation-inducing amount of an immune response-enhancing agent with cancerous B cells of a host mammal that undergo blast transformation and proliferation when contacted with an immune response-enhancing agent;
(b) maintaining said contact under biological culture conditions for a time period sufficient for said contacted cancerous B cells to proliferate and form blasts, and for the contacted cancerous B cells to die;

said immune response-enhancing agent having a structure that corresponds to a formula

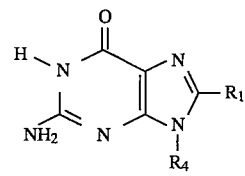

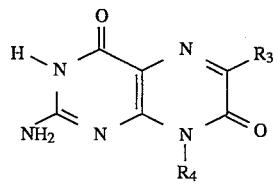

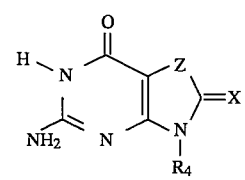

wherein

Z is O, S or N—$R_2$;

$R_1$ contains up to about 20 atoms and has a Hammett substituent sigma constant for ionization of a meta-substituted benzoic acid that is greater than that of hydrogen;

$R_2$ is a radical having a length up to about that of an n-decyl group that is selected from the group consisting of $C_1$–$C_{10}$ alkyl, $C_3$–$C_{10}$ beta-alkenyl, phenyl-substituted $C_3$–$C_6$ beta-alkenyl, benzyl, $C_1$–$C_6$ alkoxybenzyl, nitrobenzyl, hydroxy $C_1$–$C_{10}$ alkyl, polyhydroxy $C_1$–$C_{10}$ alkyl, halo $C_1$–$C_{10}$ alkyl, polyhalo $C_1$–$C_{10}$ alkyl, $C_1$–$C_6$ alkylene $C_1$–$C_6$ alkylcarboxylate, $C_1$–$C_{10}$ alkanoyl, $C_1$–$C_6$ alkoxy $C_1$–$C_6$ alkylenecarbonyl, and $C_1$–$C_6$ alkylenecarboxamido in which the carboxamido group has the formula $CONR_9R_{10}$ wherein $R_9$ and $R_{10}$ are the same or different and are selected from the group consisting of hydrogen and $C_1$–$C_6$ alkyl or $NR_9R_{10}$ together form a heterocyclic ring having five or six atoms in the ring;

X is oxygen or sulfur;

$R_3$ is a radical selected from the group consisting of hydrogen, $C_1$–$C_6$ alkyl, hydroxy $C_1$–$C_6$ alkyl, polyhydroxy $C_1$–$C_6$ alkyl, phenyl, phenyl-$C_1$–$C_6$ alkylene, $C_1$–$C_6$ alkylphenyl, $C_1$–$C_6$ alkoxyphenyl, halophenyl, trifluoromethylphenyl, hydroxy, oxo (O=), $C_1$–$C_6$ alkoxy, phenyl-$C_1$–$C_6$ alkoxy, halo, mercapto, thioxo (S=), $C_1$–$C_6$ alkylthio, phenyl-$C_1$–$C_6$ alkylthio, $C_1$–$C_6$ alkanoyl ($C_1$–$C_6$ acyl), $C_1$–$C_6$ alkoxy carbonyl, $C_1$–$C_6$ alkylene $C_1$–$C_6$ alkylcarboxylate, $C_1$–$C_6$ alkoxy $C_1$–$C_6$ alkyl carbonyl, and $C_1$–$C_6$ alkyl carboxamido in which the carboxamido group has the formula $CONR_9R_{10}$ wherein $R_9$ and $R_{10}$ are the same or different and are selected from the group consisting of hydrogen and $C_1$–$C_6$ alkyl, or $NR_9R_{10}$ together form a heterocyclic ring having five or six atoms in the ring;

$R_4$ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl, and their O-substituted $C_1$–$C_6$ alkyl, $C_1$–$C_6$ alkanoyl, benzyl, benzoyl and $C_1$–$C_6$ acetal or ketal derivatives, an O-substituent other than an acetal or ketal, if present on one oxygen, being present on all available ring substituent oxygens;

the pharmaceutically acceptable salts of said agent; and the tautomers thereof, said immune response-enhancing agent being free from ionic charge in water at pH 7.2–7.4.

28. The process according to claim 27 wherein said immune response-enhancing agent has a structure that corresponds to a formula

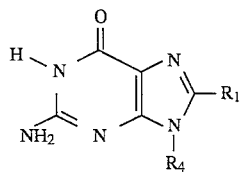

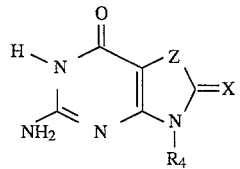

wherein Z is N—$R_2$ and =X is =O.

29. The process according to claim 28 wherein $R_4$ is 1'-aldopentosidyl in mono-deoxygenated 1'-aldopentosidyl.

30. The process according to claim 29 wherein $R_1$ is OH or SH.

31. The process according to claim 29 wherein $R_2$ is selected from the group consisting of $C_1$–$C_{10}$ alkyl, $C_3$–$C_{10}$ beta-alkenyl and halo $C_1$–$C_{10}$ alkyl.

32. The process according to claim 29 wherein said immune response-enhancing agent is 7-allyl-8-oxoguanosine, 7-(1-chloroethyl)-8-oxoguanosine or 8-mercaptoguanosine.

* * * * *